(12) United States Patent
Hueil et al.

(10) Patent No.: US 7,654,431 B2
(45) Date of Patent: *Feb. 2, 2010

(54) SURGICAL INSTRUMENT WITH GUIDED LATERALLY MOVING ARTICULATION MEMBER

(75) Inventors: Joseph C. Hueil, Loveland, OH (US); Kenneth S. Wales, Mason, OH (US); Chad P. Boudreaux, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 30 days.

This patent is subject to a terminal disclaimer.

(21) Appl. No.: 11/100,847

(22) Filed: Apr. 7, 2005

(65) Prior Publication Data

US 2006/0226196 A1 Oct. 12, 2006

Related U.S. Application Data

(63) Continuation-in-part of application No. 11/061,908, filed on Feb. 18, 2005.

(51) Int. Cl.
*A61B 1/00* (2006.01)
(52) U.S. Cl. .............. 227/175.1; 227/175.2; 227/176.1; 227/19; 227/181.1; 227/182.2; 606/139; 606/142; 606/143; 606/205; 606/206; 606/207; 606/219
(58) Field of Classification Search .............. 227/175.1, 227/175.2, 176.1, 19, 181.1, 182.2; 606/32, 606/38–42, 139–144, 170–174, 205–207
See application file for complete search history.

(56) References Cited

U.S. PATENT DOCUMENTS

| | | | |
|---|---|---|---|
| 3,506,005 A | 4/1970 | Maccarone et al. | |
| 4,331,277 A | 5/1982 | Green | |
| 4,485,817 A | 12/1984 | Swiggett | |
| 4,488,523 A | 12/1984 | Shichman | |
| 4,794,912 A | 1/1989 | Lia | |
| 4,921,482 A | 5/1990 | Hammerslag et al. | |
| 5,005,754 A | 4/1991 | Van Overloop | |
| 5,018,657 A | 5/1991 | Pedlick et al. | |
| 5,179,934 A * | 1/1993 | Nagayoshi et al. | 600/152 |
| 5,197,649 A | 3/1993 | Bessler et al. | |
| 5,219,111 A | 6/1993 | Bilotti et al. | |
| 5,250,074 A | 10/1993 | Wilk et al. | |

(Continued)

FOREIGN PATENT DOCUMENTS

EP 0 324 635 7/1989

(Continued)

OTHER PUBLICATIONS

EPO Search Report, Application No. 06 25 0869, Jun. 19, 2006, pp. 1-4.

(Continued)

*Primary Examiner*—Rinaldi I. Rada
*Assistant Examiner*—Michelle Lopez

(57) ABSTRACT

A surgical instrument particularly suited to endoscopic use articulates an end effector by including a laterally sliding member in a proximal portion of a shaft that pivots the end effector to a selected side. Differentially opposing actuating forces (e.g., hydraulic, fluidic, mechanical) act against the laterally sliding member without binding by incorporating guidance mechanisms between the laterally sliding member and a frame of the shaft.

7 Claims, 20 Drawing Sheets

U.S. PATENT DOCUMENTS

| | | | |
|---|---|---|---|
| 5,275,608 A | 1/1994 | Forman et al. | |
| 5,312,023 A | 5/1994 | Green et al. | |
| 5,314,466 A | 5/1994 | Stern et al. | |
| 5,339,723 A | 8/1994 | Huitema | |
| 5,361,583 A | 11/1994 | Huitema | |
| 5,405,344 A | 4/1995 | Williamson et al. | |
| 5,409,498 A | 4/1995 | Braddock et al. | |
| 5,411,508 A | 5/1995 | Bessler et al. | |
| 5,411,519 A * | 5/1995 | Tovey et al. | 606/207 |
| 5,456,401 A | 10/1995 | Green et al. | |
| 5,456,684 A | 10/1995 | Schmidt et al. | |
| 5,465,895 A | 11/1995 | Knodel et al. | |
| 5,485,952 A | 1/1996 | Fontayne | |
| 5,518,164 A | 5/1996 | Hooven | |
| 5,520,678 A | 5/1996 | Heckele et al. | |
| 5,547,117 A | 8/1996 | Hamblin et al. | |
| 5,562,682 A | 10/1996 | Oberlin et al. | |
| 5,575,799 A | 11/1996 | Bolanos et al. | |
| 5,588,623 A | 12/1996 | Leduc | |
| 5,620,649 A | 4/1997 | Trotta | |
| 5,632,433 A | 5/1997 | Grant et al. | |
| 5,662,662 A | 9/1997 | Bishop et al. | |
| 5,669,544 A | 9/1997 | Schulze et al. | |
| 5,673,840 A | 10/1997 | Schulze et al. | |
| 5,673,841 A | 10/1997 | Schulze et al. | |
| 5,690,269 A | 11/1997 | Bolanos et al. | |
| 5,692,668 A * | 12/1997 | Schulze et al. | 227/175.1 |
| 5,702,408 A | 12/1997 | Wales et al. | |
| 5,743,456 A | 4/1998 | Jones et al. | |
| 5,752,973 A | 5/1998 | Kieturakis | |
| 5,779,727 A | 7/1998 | Orejola et al. | |
| 5,782,859 A | 7/1998 | Nicholas et al. | |
| 5,797,536 A | 8/1998 | Smith et al. | |
| 5,797,537 A | 8/1998 | Oberlin et al. | |
| 5,826,776 A * | 10/1998 | Schulze et al. | 227/176.1 |
| 5,829,662 A | 11/1998 | Allen et al. | |
| 5,860,995 A | 1/1999 | Berkelaar | |
| 5,865,361 A | 2/1999 | Milliman et al. | |
| 5,901,895 A | 5/1999 | Heaton et al. | |
| 5,918,791 A | 7/1999 | Sorrentino et al. | |
| 6,010,054 A | 1/2000 | Johnson et al. | |
| 6,460,749 B1 | 10/2002 | Levinson et al. | |
| 6,485,409 B1 | 11/2002 | Voloshin et al. | |
| 6,488,197 B1 | 12/2002 | Whitman | |
| 6,506,202 B1 | 1/2003 | Dutta et al. | |
| 6,666,854 B1 | 12/2003 | Lange | |
| 6,667,825 B2 | 12/2003 | Lu et al. | |
| 6,669,073 B2 | 12/2003 | Milliman et al. | |
| 6,715,259 B2 | 4/2004 | Johnston et al. | |
| 6,755,338 B2 | 6/2004 | Hahnen et al. | |
| 6,756,094 B1 | 6/2004 | Wang et al. | |
| 6,786,382 B1 | 9/2004 | Hoffman | |
| 6,830,174 B2 | 12/2004 | Hillstead et al. | |
| 6,877,647 B2 | 4/2005 | Green et al. | |
| 6,905,057 B2 * | 6/2005 | Swayze et al. | 227/176.1 |
| 6,951,675 B2 | 10/2005 | Chin et al. | |
| 6,953,139 B2 * | 10/2005 | Milliman et al. | 227/175.1 |
| 6,964,363 B2 | 11/2005 | Wales et al. | |
| 6,978,921 B2 | 12/2005 | Shelton | |
| 6,981,628 B2 | 1/2006 | Wales | |
| 7,087,052 B2 | 8/2006 | Sampson et al. | |
| 7,111,769 B2 | 9/2006 | Wales et al. | |
| 7,112,357 B2 | 9/2006 | Miller et al. | |
| 7,166,077 B2 | 1/2007 | Millay et al. | |
| 7,213,736 B2 | 5/2007 | Wales et al. | |
| 7,407,074 B2 | 8/2008 | Ortiz et al. | |
| 7,410,086 B2 | 8/2008 | Ortiz et al. | |
| 7,481,824 B2 | 1/2009 | Gillum et al. | |
| 2003/0045900 A1 | 3/2003 | Hahnen et al. | |
| 2003/0111507 A1 | 6/2003 | Nunez | |
| 2003/0178848 A1 | 9/2003 | Williams et al. | |
| 2004/0002726 A1 | 1/2004 | Nunez et al. | |
| 2004/0108357 A1 | 6/2004 | Milliman et al. | |
| 2004/0173659 A1 | 9/2004 | Green et al. | |
| 2004/0179244 A1 | 9/2004 | Lai et al. | |
| 2004/0232196 A1 | 11/2004 | Shelton et al. | |
| 2004/0232197 A1 | 11/2004 | Shelton et al. | |
| 2004/0232201 A1 | 11/2004 | Wenchell et al. | |
| 2004/0243176 A1 | 12/2004 | Hahnen et al. | |
| 2005/0006429 A1 | 1/2005 | Wales et al. | |
| 2005/0006430 A1 | 1/2005 | Wales | |
| 2005/0006432 A1 | 1/2005 | Racenet et al. | |
| 2005/0006434 A1 * | 1/2005 | Wales et al. | 227/180.1 |
| 2005/0070958 A1 | 3/2005 | Swayze et al. | |
| 2005/0107824 A1 | 5/2005 | Hillstead et al. | |
| 2005/0165415 A1 * | 7/2005 | Wales | 606/139 |
| 2005/0263562 A1 | 12/2005 | Shelton | |
| 2006/0011699 A1 | 1/2006 | Olson et al. | |
| 2006/0016853 A1 | 1/2006 | Racenet | |
| 2006/0022014 A1 | 2/2006 | Shelton, IV et al. | |
| 2006/0022015 A1 | 2/2006 | Shelton, IV et al. | |
| 2006/0025809 A1 | 2/2006 | Shelton, IV | |
| 2006/0025813 A1 | 2/2006 | Shelton et al. | |
| 2006/0025817 A1 | 2/2006 | Ortiz et al. | |
| 2006/0041273 A1 | 2/2006 | Ortiz et al. | |
| 2006/0047307 A1 * | 3/2006 | Ortiz et al. | 606/219 |
| 2006/0047308 A1 | 3/2006 | Ortiz et al. | |
| 2006/0089535 A1 | 4/2006 | Raz et al. | |
| 2006/0190028 A1 | 8/2006 | Wales et al. | |
| 2006/0190032 A1 | 8/2006 | Wales | |
| 2006/0226196 A1 | 10/2006 | Hueil et al. | |
| 2006/0229665 A1 | 10/2006 | Wales et al. | |
| 2006/0289600 A1 | 12/2006 | Wales | |
| 2007/0027468 A1 | 2/2007 | Wales et al. | |

FOREIGN PATENT DOCUMENTS

| | | |
|---|---|---|
| EP | 0 598 976 | 6/1994 |
| EP | 0717959 | 6/1996 |
| EP | 0769273 | 4/1997 |
| EP | 0807409 | 11/1997 |
| EP | 0 603 472 | 6/2004 |
| EP | 1495726 | 1/2005 |
| EP | 0717959 | 2/2006 |
| EP | 1627605 | 2/2006 |
| EP | 1693008 | 8/2006 |
| WO | WO 01/93766 | 12/2001 |
| WO | WO 03/013374 | 2/2003 |
| WO | WO 03/101313 | 12/2003 |
| WO | WO 2004/002327 | 1/2004 |
| WO | WO 2004/006980 | 1/2004 |
| WO | WO 2004/032762 | 4/2004 |

OTHER PUBLICATIONS

EPO Search Report, Application No. 06253759.2, pp. 1-5.
EPO Search Report, Application No. 06253759.2, Nov. 24, 2006, pp. 1-5.
Australian Search Report for Application No. SG 200600909-6, dated Mar. 2, 2007.
Australian Search Report for Application No. SG 200601987-1, dated Feb. 8, 2007.
Danish Search Report for Application No. 200601986-3, dated Apr. 11, 2007.
European Search Report dated Jul. 19, 2007 for EPO Application No. 06253226.
European Search Report dated Aug. 8, 2007 for EPO Application No. 06251959.
European Search Report dated Aug. 21, 2007 for EPO Application No. 06254005.
Office Action dated Sep. 27, 2006 for U.S. Appl. No. 11/165,094.
Office Action dated Mar. 29, 2007 for U.S. Appl. No. 11/165,094.
Office Action dated Jun. 26, 2007 for U.S. Appl. No. 11/239,528.
Office Action dated Aug. 23, 2007 for U.S. Appl. No. 11/165,094.
Office Action dated Sep. 7, 2007 for U.S. Appl. No. 11/238,358.

European Search Report dated Jul. 19, 2007 for EPO Application No. 06253226.
European Search Report dated Nov. 23, 2007 for EPO Application No. 06253224.
Notice of Allowance dated Nov. 15, 2006 for U.S. Appl. No. 11/100,847.
Notice of Allowance dated Oct. 05, 2007 for U.S. Appl. No. 11/061,908.
Notice of Allowance dated Nov. 30, 2007 for U.S. Appl. No. 11/100,847.
Office Action dated Jun. 1, 2006 for U.S. Appl. No. 11/100,847.
Office Action dated Sep. 27, 2006 for U.S. Appl. No. 11/165,094.
Office Action dated Dec. 6, 2006 for U.S. Appl. No. 11/061,908.
Office Action dated Mar. 9, 2007 for U.S. Appl. No. 11/061,908.
Office Action dated Apr. 5, 2007 for U.S. Appl. No. 11/239,528.
Office Action dated Jun. 4, 2007 for U.S. Appl. No. 11/165,094.
Office Action dated Aug. 1, 2007 for U. S. Appl. No. 11/100,847.
Office Action dated Jan. 14, 2008 for U.S. Appl. No. 11/239,528.
Notice of Allowance dated Oct. 5, 2007 for U.S. Appl. No. 11/061,908.
Notice of Allowance dated Nov. 16, 2007 for U.S. Appl. No. 11/061,908.
Notice of Allowance dated Feb. 20, 2008 for U.S. Appl. No. 11/061,908.
Notice of Allowance dated Jun. 26, 2008 for U.S. Appl. No. 11/165,094.
Notice of Allowance dated Jul. 31, 2008 for U.S. Appl. No. 11/238,358.
Final Rejection dated Feb. 25, 2008 for U.S. Appl. No. 11/165,094.
Final Rejection dated Mar. 26, 2008 for U.S. Appl. No. 11/238,358.
Non-Final Rejection dated Apr. 7, 2008 for U.S. Appl. No. 11/165,468.
Non-Final Rejection dated Jul. 11, 2008 for U.S. Appl. No. 11/239,528.
Non-Final Rejection dated Jul. 17, 2008 for U.S. Appl. No. 11/100,772.
European Search Report dated Nov. 29, 2006 for Application No. 06254005.9
EPO Search Report dated Jul. 28, 2006 for Application No. 06253224.
EPO Search Report dated Aug. 31, 2006 for Application No. 06253226.
EPO Search Report dated Nov. 6, 2006 for Application No. 06253759.
EPO Search Report dated Nov. 20, 2006 for Application No. 06254005.
EPO Search Report dated May 5, 2008 for Application No. 06251960.

* cited by examiner

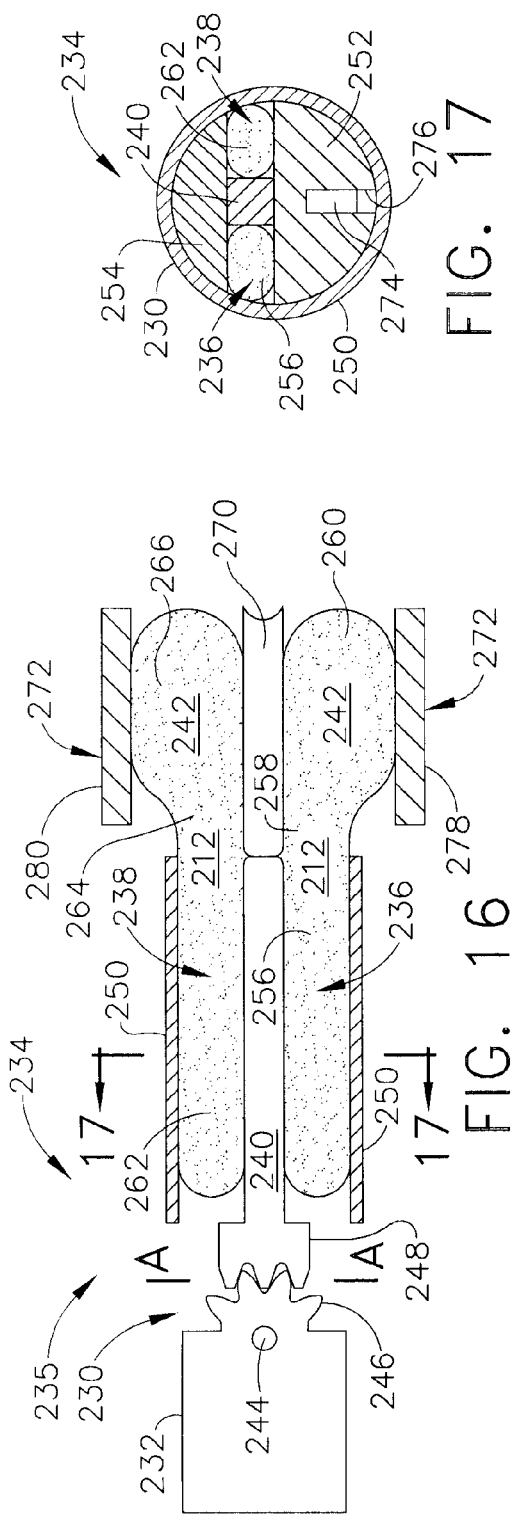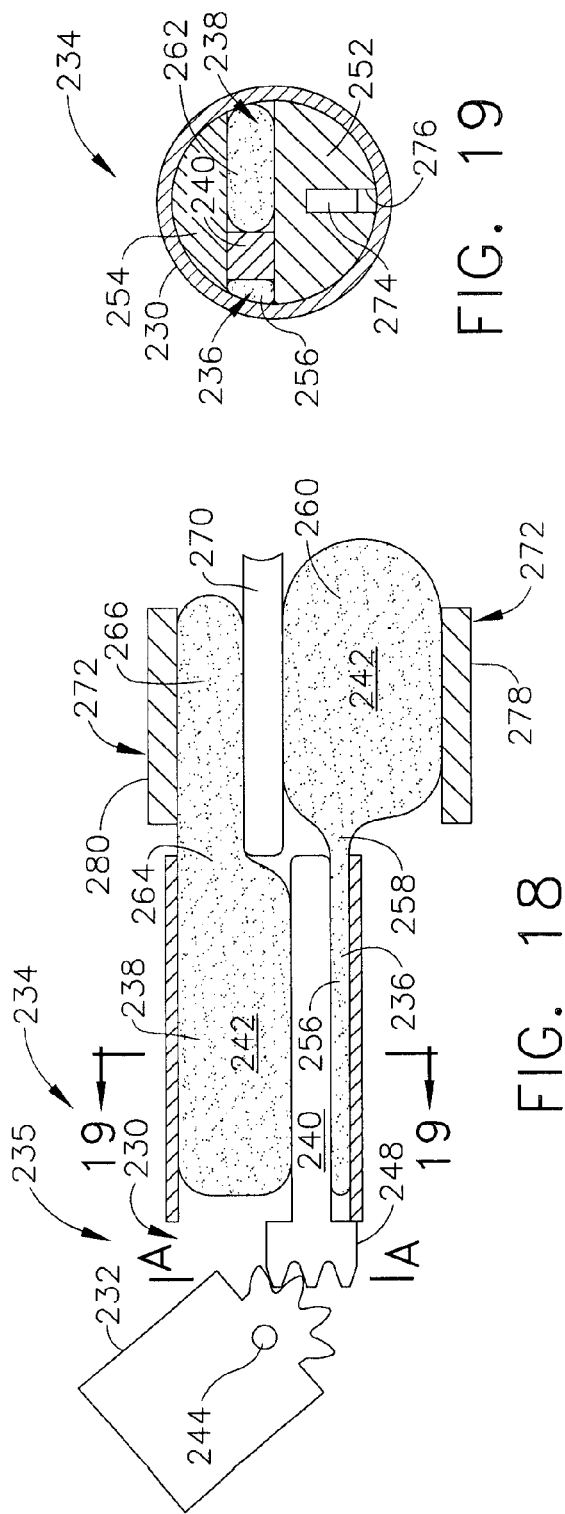

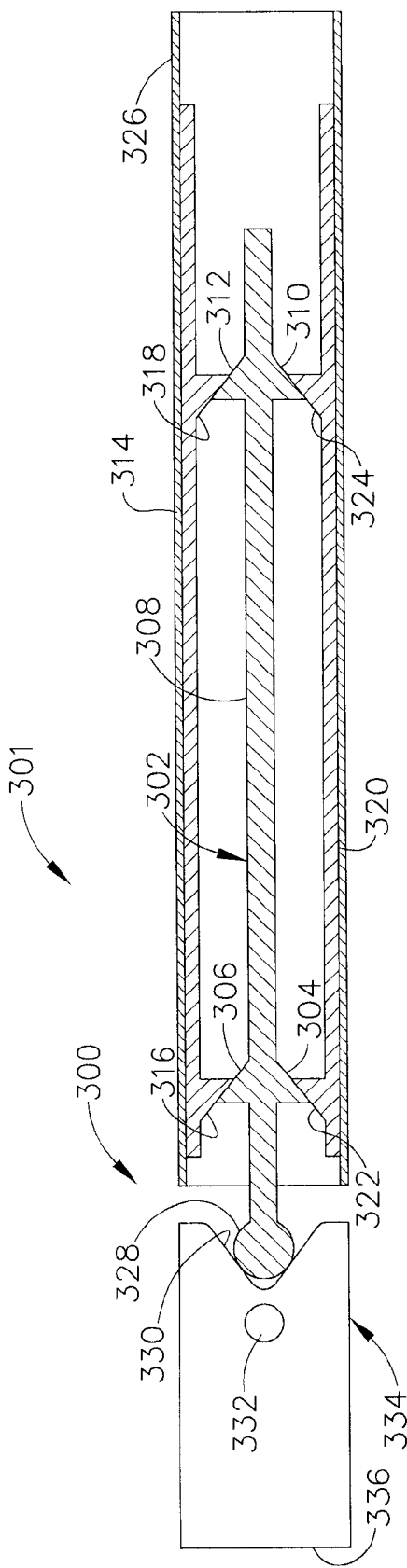
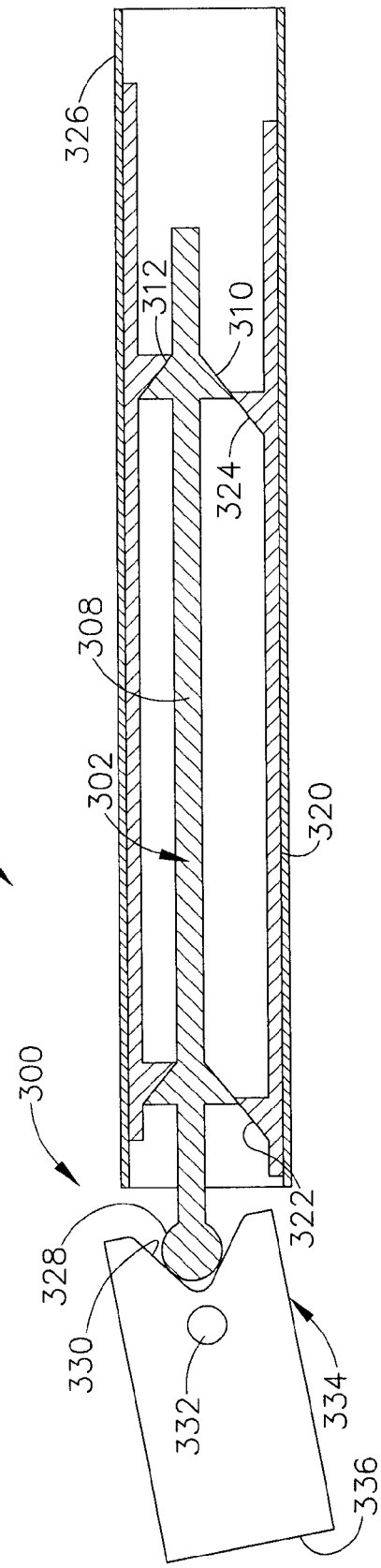

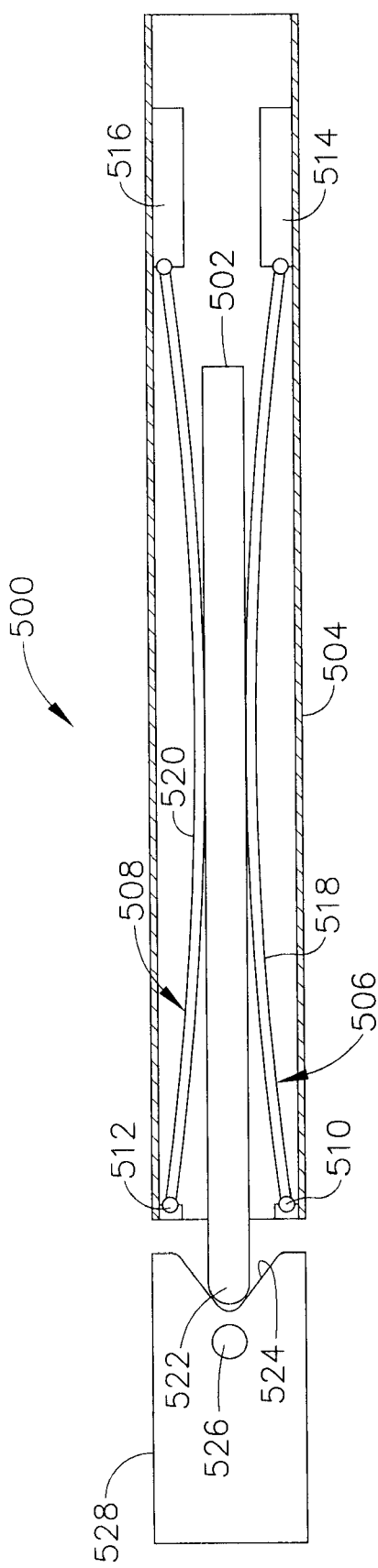
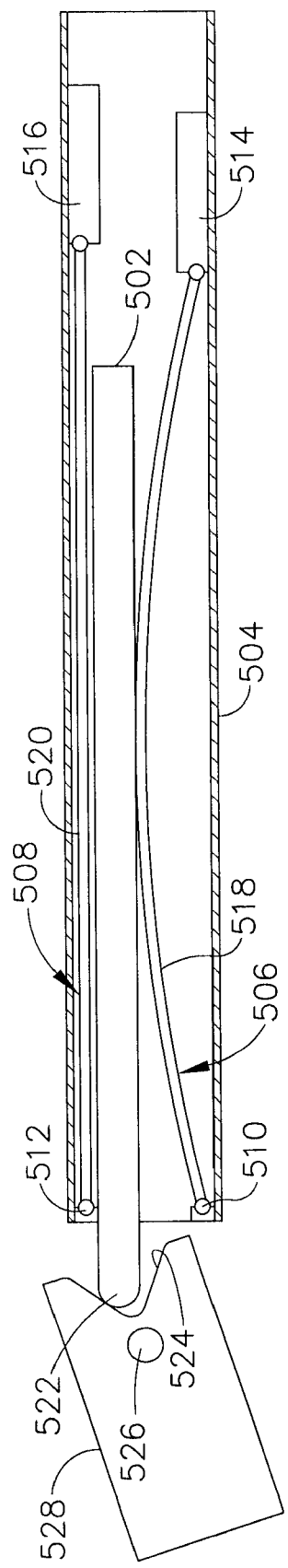
FIG. 24
FIG. 25

SURGICAL INSTRUMENT WITH GUIDED LATERALLY MOVING ARTICULATION MEMBER

CROSS REFERENCE TO RELATED APPLICATIONS

The present invention is a continuation-in-part application of commonly owned U.S. patent application Ser. No. 11/061,908 entitled "SURGICAL INSTRUMENT INCORPORATING A FLUID TRANSFER CONTROLLED ARTICULATION MECHANISM" to Kenneth Wales and Chad Boudreaux filed on Feb. 18, 2005, the disclosure of which is hereby incorporated by reference in its entirety.

FIELD OF THE INVENTION

The present invention relates in general to surgical instruments that are suitable for endoscopically inserting an end effector (e.g., endocutter, grasper, cutter, staplers, clip applier, access device, drug/gene therapy delivery device, and an energy device using ultrasound, RF, laser, etc.) to a surgical site, and more particularly to such surgical instruments with an articulating shaft.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Positioning the end effector is constrained by the trocar. Generally, these endoscopic surgical instruments include a long shaft between the end effector and a handle portion manipulated by the clinician. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

More recently, U.S. patent Ser. No. 10/443,617, "SURGICAL STAPLING INSTRUMENT INCORPORATING AN E-BEAM FIRING MECHANISM" to Shelton IV et al., filed on 20 May 2003, which is hereby incorporated by reference in its entirety, describes an improved "E-beam" firing bar for severing tissue and actuating staples. Some of the additional advantages include affirmatively spacing the jaws of the end effector, or more specifically a staple applying assembly, even if slightly too much or too little tissue is clamped for optimal staple formation. Moreover, the E-beam firing bar engages the end effector and staple cartridge in a way that enables several beneficial lockouts to be incorporated.

Depending upon the nature of the operation, it may be desirable to further adjust the positioning of the end effector of an endoscopic surgical instrument. In particular, it is often desirable to orient the end effector at an axis transverse to the longitudinal axis of the shaft of the instrument. The transverse movement of the end effector relative to the instrument shaft is conventionally referred to as "articulation". This is typically accomplished by a pivot (or articulation) joint being placed in the extended shaft just proximal to the staple applying assembly. This allows the surgeon to articulate the staple applying assembly remotely to either side for better surgical placement of the staple lines and easier tissue manipulation and orientation. This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation.

In co-pending and commonly owned U.S. patent application Ser. No. 10/615,973 "SURGICAL INSTRUMENT INCORPORATING AN ARTICULATION MECHANISM HAVING ROTATION ABOUT THE LONGITUDINAL AXIS" to Frederick E. Shelton IV et al, the disclosure of which is hereby incorporated by reference in its entirety, a rotational motion is used to transfer articulation motion as an alternative to a longitudinal motion.

While these mechanically communicated articulation motions have successfully enabled an endoscopic surgical stapling and severing instrument to articulate, development trends pose numerous challenges and barriers to entry into the market. Conflicting design objects include a shaft of as small a diameter as possible to reduce the size of the surgical opening yet with sufficient strength to perform the several motions (e.g., closing, firing, articulation, rotation, etc.). In addition, transferring sufficient force without binding and other frictional problems imposes design constraints that limit desirable features and reliability.

Consequently, a significant need exists for an articulating surgical instrument that incorporates an articulation mechanism that employs an articulation force that may be incorporated within the close confines thereof without interfering with the firing and closing motions.

BRIEF SUMMARY OF THE INVENTION

The invention overcomes the above-noted and other deficiencies of the prior art by providing a surgical instrument having an articulating shaft attached between a handle and an end effector that uses a laterally sliding member in the proximal portion of the shaft that acts against a pivoting feature of the end effector. Laterally moving actuators on opposing sides of the laterally sliding member control the pivoting to each side. This laterally moving member presents a large longitudinal surface area to act upon. Advantageously, a frame of the shaft that support moving components therein includes a lateral guide mechanism that engages the lateral sliding member, thus avoiding binding that may otherwise impair performance.

In one aspect of the invention, a surgical instrument includes a proximal portion that is manipulated external to a patient to position an attached elongate shaft and end effector to a desired surgical site inside of the patient. An articulation joint attaches the end effector to the elongate shaft to give further clinical flexibility in reaching tissue at a desired angle. An articulation control, which is attached to the proximal portion, transfers a differential longitudinal motion down the shaft to cooperatively act upon respective sides of the laterally sliding member. A lateral channel formed in one of the frame or lateral sliding member is engaged by a corresponding lateral track formed in the other. Thereby, the lateral sliding member is prevented from being actuated in an angled orientation other than aligned with the longitudinal axis of the shaft.

In another aspect of the invention, expansive and compressive bladders oppose each side of the laterally sliding member.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above and the detailed description of the embodiments given below, serve to explain the principles of the present invention.

FIG. 16 is a diagram of a laterally moving fluidic articulation mechanism with rack and gear segment pivoting depicted in a nonarticulated state.

FIG. 17 is cross section front view in elevation of the fluidic articulation mechanism of FIG. 16 taken along lines 17—17.

FIG. 18 is a diagram of the laterally moving fluidic articulation mechanism with a rack and gear segment pivoting depicted in an articulated state.

FIG. 19 is cross section front view in elevation of the fluidic articulation mechanism of FIG. 18 taken along lines 19—19.

FIG. 20 is a top diagrammatic view of a surgical instrument articulated by at least one longitudinally moving member that laterally cams a slide bar, which in turn articulates an end effector.

FIG. 21 is a top diagrammatic view of the surgical instrument of FIG. 20 in an articulated state.

FIG. 24 is a top diagrammatic view of a surgical instrument having a slide bar laterally positioned by a pair of buckling members, each with a longitudinally adjustable proximal endpoint, to articulate an end effector.

FIG. 25 is a top diagrammatic view of the surgical instrument of FIG. 24 depicted in an articulated state.

DETAILED DESCRIPTION OF THE INVENTION

Overview of Articulating Shaft

Figure 1:
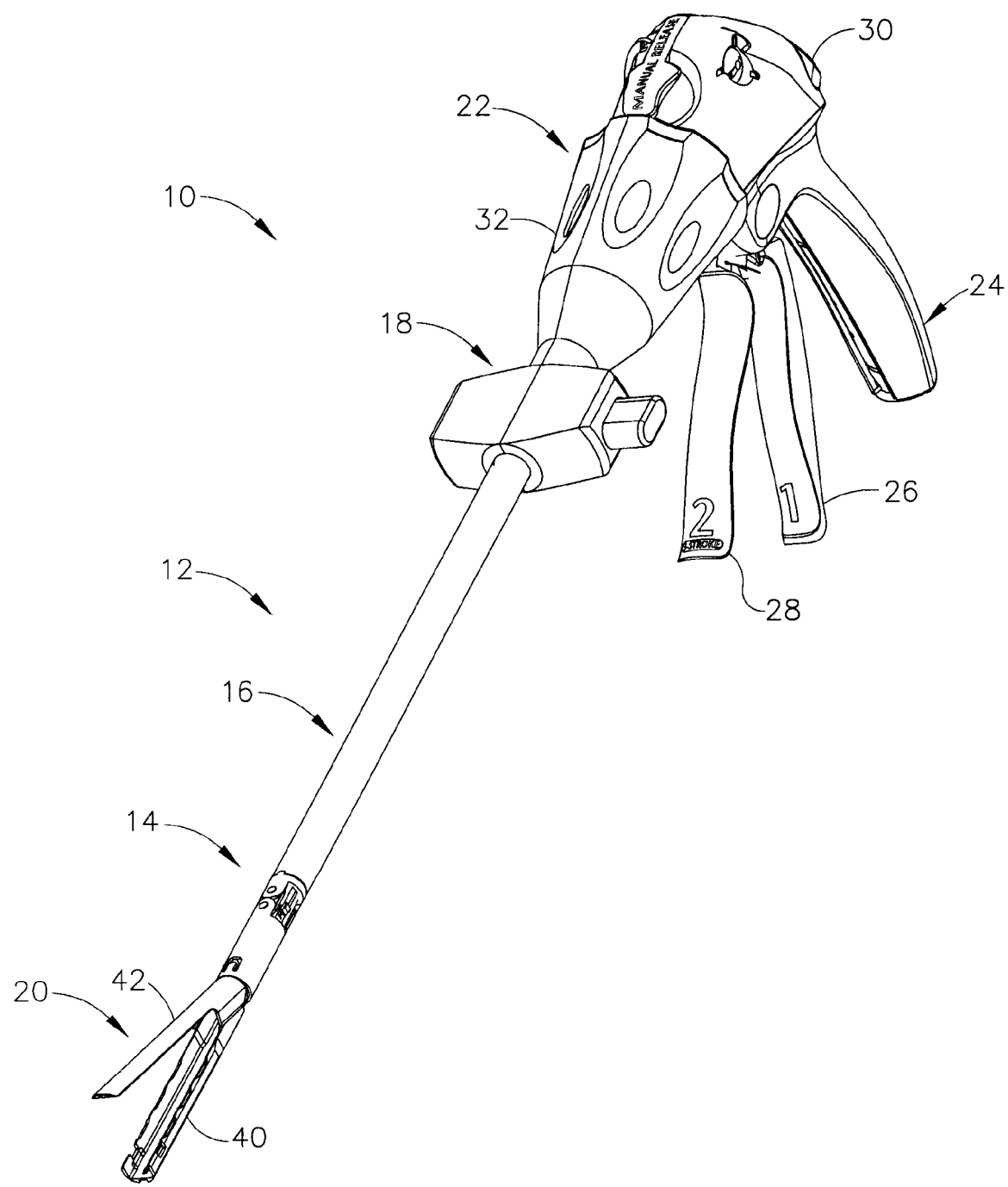
FIG. 1 is a front top perspective view of a surgical stapling and severing instrument shown with an open end effector, or staple applying assembly, and with the staple cartridge removed.
Figure 2:
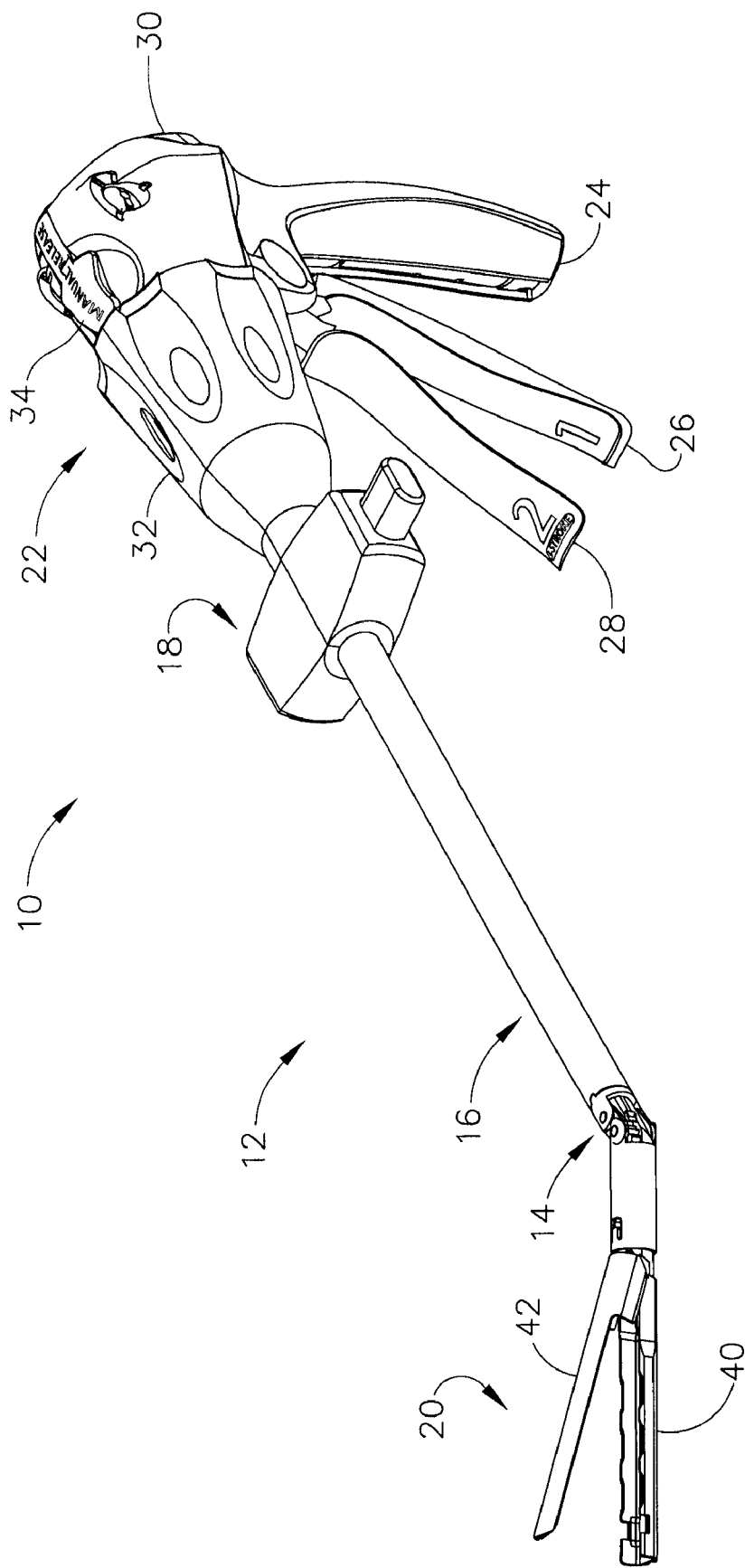
FIG. 2 is a front top perspective view of the surgical stapling and severing instrument of FIG. 1 with an articulation mechanism actuated by a fluidic actuation control.

Turning to the Drawings, wherein like numerals denote like components throughout the several views, FIG. 1 depicts a surgical instrument, which in the illustrative versions is more particularly a surgical stapling and severing instrument 10, that is capable of practicing the unique benefits of the present invention. In particular, the surgical stapling and severing instrument 10 is sized for insertion, in a nonarticulated state as depicted in FIG. 1, through a trocar cannula passageway to a surgical site in a patient (not shown) for performing a surgical procedure. Once an implement portion 12 is inserted through a cannula passageway, an articulation mechanism 14 incorporated into a distal portion of an elongate shaft 16 of the implement portion 12 may be remotely articulated, as depicted in FIG. 2, by an articulation control 18. An end effector, depicted in the illustrative version as a staple applying assembly 20, is distally attached to the articulation mechanism 14. Thus, remotely articulating the articulation mechanism 14 thereby articulates the staple applying assembly 20 from a longitudinal axis of the elongate shaft 16. Such an angled position may have advantages in approaching tissue from a desired angle for severing and stapling, approaching tissue otherwise obstructed by other organs and tissue, and/or allowing an endoscope to be positioned behind and aligned with the staple applying assembly 20 for confirming placement.

Handle

The surgical and stapling and severing instrument 10 includes a handle portion 22 proximally connected to the implement portion 12 for providing positioning, articulation, closure and firing motions thereto. The handle portion 22 includes a pistol grip 24 toward which a closure trigger 26 is pivotally and proximally drawn by the clinician to cause clamping, or closing, of the staple applying assembly 20. A firing trigger 28 is farther outboard of the closure trigger 26 and is pivotally drawn by the clinician to cause the stapling and severing of tissue clamped in the staple applying assembly 20. Thereafter, a closure release button 30 is depressed to release the clamped closure trigger 26, and thus the severed and stapled ends of the clamped tissue. The handle portion 22 also includes a rotation knob 32 coupled for movement with the elongate shaft 16 to rotate the shaft 16 and the articulated staple applying assembly 20 about the longitudinal axis of the shaft 16. The handle portion 22 also includes a firing retraction handle 34 to assist in retracting a firing mechanism (not depicted in FIGS. 1–2) should binding occur, so that opening of the staple applying assembly 20 may occur thereafter.

It will be appreciated that the terms "proximal" and "distal" are used herein with reference to a clinician gripping a handle of an instrument. Thus, the surgical stapling assembly 20 is distal with respect to the more proximal handle portion 22. It will be further appreciated that for convenience and clarity, spatial terms such as "vertical" and "horizontal" are used herein with respect to the drawings. However, surgical instruments are used in many orientations and positions, and these terms are not intended to be limiting and absolute.

An illustrative multi-stroke handle portion 22 for the surgical stapling and severing instrument 10 of FIGS. 1–2 is described in greater detail in the co-pending and commonly-owned U.S. patent application entitled "SURGICAL STAPLING INSTRUMENT INCORPORATING A MULTI-STROKE FIRING POSITION INDICATOR AND RETRACTION MECHANISM" to Swayze and Shelton IV, Ser. No. 10/674,026, the disclosure of which is hereby incorporated by reference in its entirety, with additional features and variation as described herein. While a multi-stroke handle portion 22 advantageously supports applications with high firing forces over a long distance, applications consistent with the present invention may incorporate a single firing stroke, such as described in co-pending and commonly owned U.S. patent application "SURGICAL STAPLING INSTRUMENT HAVING SEPARATE DISTINCT CLOSING AND FIRING SYSTEMS" to Frederick E. Shelton IV, Michael E. Setser, and Brian J. Hemmelgam, Ser. No. 10/441,632, the disclosure of which is hereby incorporated by reference in its entirety.

Implement Portion (Articulating Elongate Shaft and Staple Applying Assembly)

Figure 3:
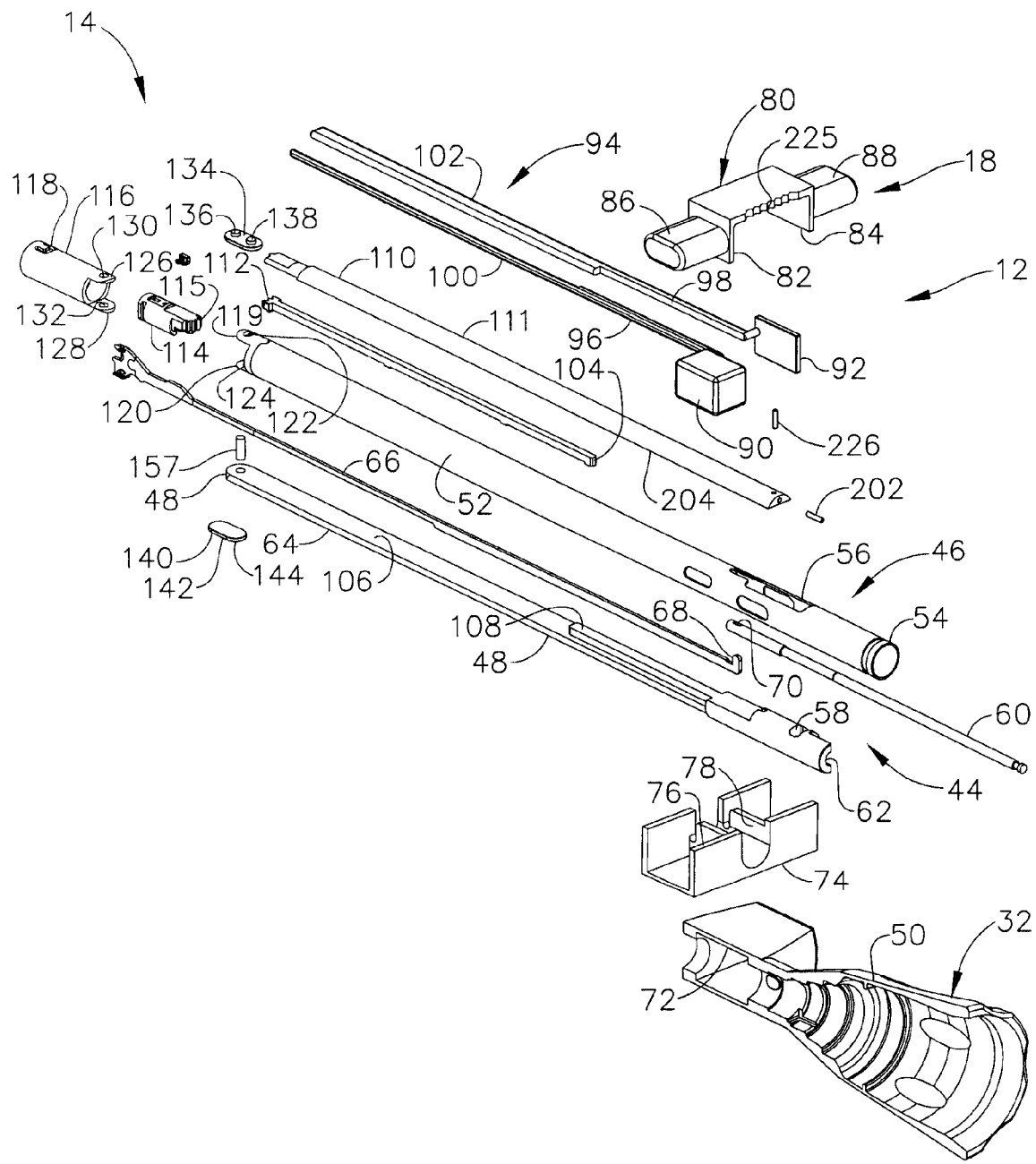
FIG. 3 is a perspective disassembled view of an elongate shaft and articulation mechanism of the surgical stapling and severing instrument of FIG. 1.
Figure 4:
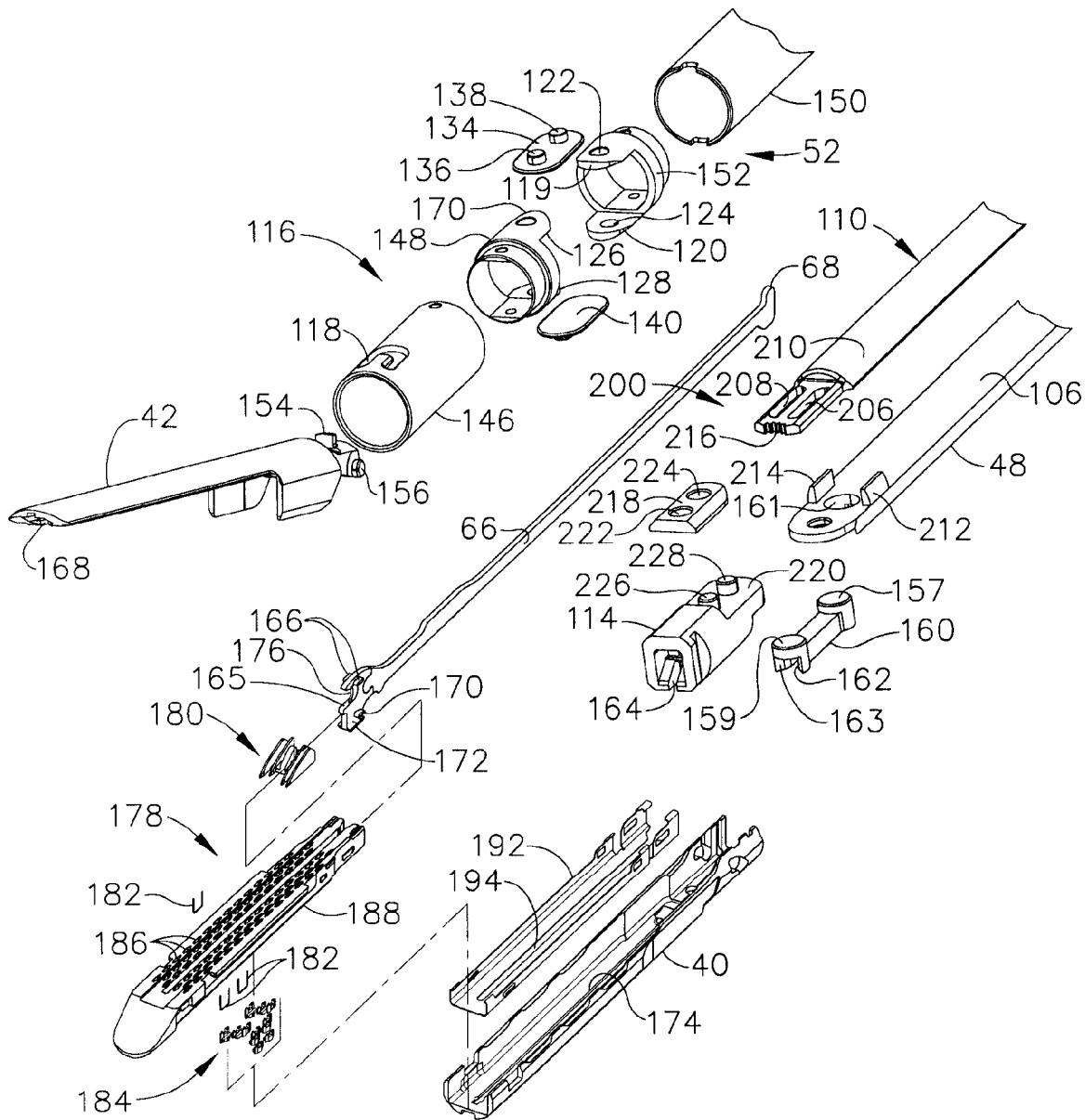
FIG. 4 is a perspective disassembled view of distal portions of an implement portion of the surgical stapling and severing instrument of FIG. 1, including the staple applying assembly and articulation mechanism.
Figure 5:
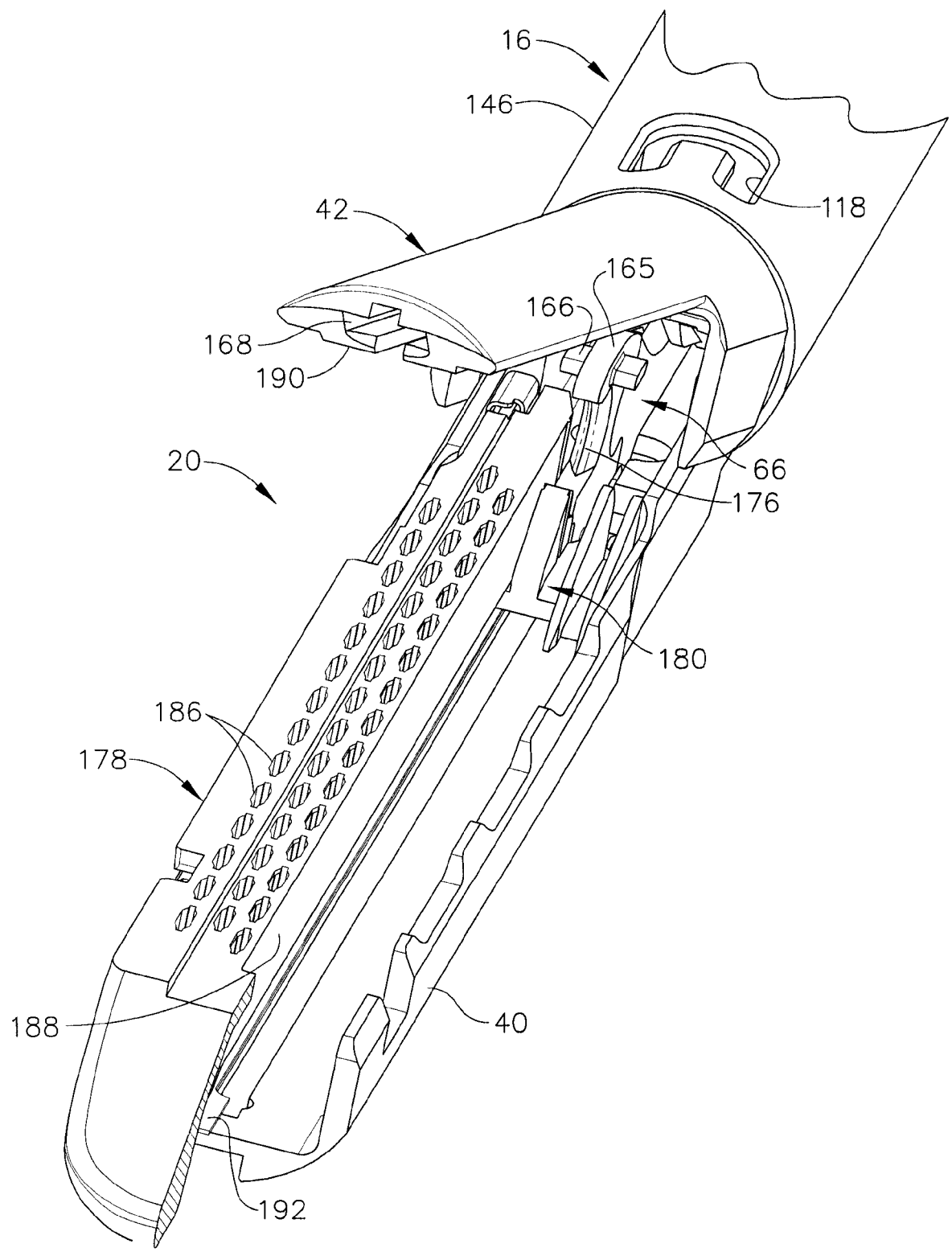
FIG. 5 is a top perspective view of the staple applying assembly of FIGS. 1 and 4 with a lateral half of a staple cartridge removed to expose components driven by a firing motion.

In FIGS. 3–5, the implement portion 12 advantageously incorporates the multiple actuation motions of longitudinal rotation, articulation, closure and firing within a small diameter suitable for endoscopic and laparoscopic procedures. The staple applying assembly 20 ("end effector") has a pair of pivotally opposed jaws, depicted as an elongate channel 40 with a pivotally attached anvil 42 (FIGS. 1–2, 4–5). Closure and clamping of the anvil 42 to the elongate channel 40 is achieved by longitudinally supporting the elongate channel 40 with a frame assembly 44 (FIG. 3) rotatingly attached to the handle portion 22 over which a double pivot closure sleeve assembly 46 longitudinally moves to impart a closing and opening respectively to a distal and proximal motion to the anvil 42, even with the staple applying assembly 20 articulated as in FIG. 2.

With particular reference to FIG. 3, the frame assembly 44 includes a single pivot frame ground 48 whose proximal end is engaged to the rotation knob 32, with a right half shell 50 thereon shown in FIG. 3. It should be appreciated that a proximal end of the closure sleeve assembly 46, specifically of a closure straight tube 52, encompasses the proximal end of the frame ground 48, passing further internally to the handle portion 22 to engage closure components (not shown) that longitudinally translate the closure sleeve assembly 46. A circular lip 54 at the proximal end of the closure straight tube 52 provides a rotating engagement to such components. Engaging components of the rotation knob 32 pass through a longitudinal slot 56 on a proximal portion of the straight closure tube 52 to engage an aperture 58 proximally positioned on the frame ground 48. The longitudinal slot 56 is of sufficient length to allow the closure longitudinal translation of the closure sleeve assembly 46 at various rotational angles set by the rotation knob 32 to the closure sleeve assembly 46 and the frame ground 48.

The elongate shaft 16 supports the firing motion by receiving a firing rod 60 that rotatingly engages firing components of the handle portion 22 (not shown). The firing rod 60 enters a proximal opening 62 along the longitudinal centerline of the frame ground 48. The distal portion of the frame ground 48 includes a firing bar slot 64 along its bottom that communicates with the proximal opening 62. A firing bar 66 longitudinally translates in the firing bar slot 64 and includes an upwardly projecting proximal pin 68 that engages a distal end 70 of the firing rod 60.

The elongate shaft 16 supports articulation by incorporating a rectangular reservoir cavity 72, one lateral portion depicted in a distal portion of the rotation knob 32. A bottom compartment 74 that resides within the rectangular reservoir cavity 72 has laterally spaced apart left and right baffles 76, 78. An articulation actuator 80 slides laterally overtop of the bottom compartment 74, its downward laterally spaced left and right flanges 82, 84, which are outboard of the baffles 76, 78, each communicating laterally to left and right push buttons 86, 88 that extend outwardly from the respective shell halves of the rotation knob 32. The lateral movement of the articulation actuator 80 draws left and right flanges 82, 84 nearer and farther respectively to the left and right baffles 76, 78, operating against left and right reservoir bladders 90, 92 of a fluidic articulation system 94, each bladder 90, 92 communicating respectively and distally to left and right fluid conduits or passageways 96, 98 that in turn communicate respectively with left and right actuating bladders 100, 102. The latter oppose and laterally pivot a T-bar 104 of the articulation mechanism 14.

The frame assembly 44 constrains these fluidic actuations by including a top and distal recessed table 106 of the frame ground 48 upon which resides the fluid passages 96, 98 and actuating bladders 100, 102. The T-bar 104 also slidingly resides upon the recessed table 106 between the actuating bladders 100, 102. Proximal to the T-bar 104, a raised barrier rib 108 is aligned thereto, serving to prevent inward expansion of the fluid passages 96, 98. The frame assembly 44 has a rounded top frame cover (spacer) 110 that slides overtop of the frame ground 48, preventing vertical expansion of the fluid passages 96, 98 and actuating bladders 100, 102, as well as constraining any vertical movement of the T-bar 104. In particular, the frame cover 110 includes features that enable it to also provide an articulation locking member 111, described in greater detail below as part of an articulation locking mechanism 113.

A distal end ("rack") 112 of the T-bar 104 engages to pivot a proximally directed gear segment 115 of an articulated distal frame member 114 of the articulation mechanism 14. An articulated closure ring 116 encompasses the articulated frame member 14 and includes a horseshoe aperture 118 that engages the anvil 42. A double pivoting attachment is formed between the closure straight tube 52 and articulating closure ring 116 over the articulating mechanism 14, allowing longitudinal closure motion even when the articulating mechanism 14 is articulated. In particularly, top and bottom distally projecting pivot tabs 118, 120 on the closure straight tube 52 having pin holes 122, 124 respectively are longitudinally spaced away from corresponding top and bottom proximally projecting pivot tabs 126, 128 on the articulating closure ring 116 having pin holes 130, 132 respectively. An upper double pivot link 134 has longitudinally spaced upwardly directed distal and aft pins 136, 138 that engage pin holes 122, 130 respectively and a lower double pivot link 140 has longitudinally spaced downwardly projecting distal and aft pins 142, 144 that engage pin holes 124, 132 respectively.

With particular reference to FIG. 4, the articulating closure ring 116 is shown for enhanced manufacturability to include a short tube 146 attached to an articulating attachment collar 148 that includes the proximally projecting pivot tabs 126, 128. Similarly, the straight closure tube 52 is assembled from a long closure tube 150 that attaches to an aft attachment collar 152 that includes the distally projecting pivot tabs 118, 120. The horseshoe aperture 118 in the short closure tube 146 engages an upwardly projecting anvil feature 154 slightly proximal to lateral pivot pins 156 that engage pivot recesses 158 inside of the elongate channel 40.

The illustrative version of FIG. 4 includes a dog bone link 160 whose proximal pin 157 pivotally attaches to the frame ground 48 in a frame hole 161 and whose proximal pin 159 rigidly attaches to a proximal undersurface 162 of the articulating frame member 114, thereby providing pivotal support there between. A bottom longitudinal knife slot 163 in the dog bone link 160 guides an articulating portion of the firing bar 66. The articulating frame member 114 also includes a bottom longitudinal slot 164 for guiding a distal portion of the firing bar 66.

Staple Applying Apparatus (End Effector)

With reference to FIGS. 4-5, the firing bar 66 distally terminates in an E-beam 165 that includes upper guide pins 166 that enter an anvil slot 168 in the anvil 42 to verify and assist in maintaining the anvil 42 in a closed state during staple formation and severing. Spacing between the elongate channel 40 and anvil 42 is further maintained by the E-beam 164 by having middle pins 170 slide along the top surface of the elongate channel 40 while a bottom foot 172 opposingly slides along the undersurface of the elongate channel 40, guided by a longitudinal opening 174 in the elongate channel 40. A distally presented cutting surface 176 of the E-beam 164, which is between the upper guide pins 166 and middle pin 170, severs clamped tissue while the E-beam actuates a replaceable staple cartridge 178 by distally moving a wedge sled 180 that causes staple drivers 182 to cam upwardly driving staples 184 out of upwardly open staple holes 186 in a staple cartridge body 188, forming against a staple forming undersurface 190 of the anvil 42. A staple cartridge tray 192 encompasses from the bottom the other components of the staple cartridge 178 to hold them in place. The staple cartridge tray 192 includes a rearwardly open slot 194 that overlies the longitudinal opening 174 in the elongate channel 40, thus the middle pins 170 pass inside of the staple cartridge tray 192.

The staple applying assembly 20 is described in greater detail in co-pending and commonly-owned U.S. patent application Ser. No. 10/955,042, "ARTICULATING SURGICAL STAPLING INSTRUMENT INCORPORATING A TWO-PIECE E-BEAM FIRING MECHANISM" to Frederick E. Shelton IV, et al., filed 30 Sep. 2004, the disclosure of which is hereby incorporated by reference in its entirety.

Articulation Locking Mechanism

In FIGS. 3-4, and 6-8, an articulation lock mechanism 200 is advantageously incorporated to maintain the staple applying assembly 20 at a desired articulation angle. The articulation lock mechanism 200 reduces loads on the left and right actuating bladders 100, 102. In particular, a compression spring 202 (FIG. 3) is proximally positioned between a proximal end 204 of the articulation locking member 111 and the handle portion 22, biasing the articulation locking member 111 distally. With particular reference to FIG. 4, two parallel slots 206, 208 at a distal end 210 of the articulation locking member 111 receive respectively upwardly projecting guide ribs 212, 214 on the frame ground 48. The guide ribs 212, 214 are longitudinally shorter than the parallel slots 206, 208 allowing a range of relative longitudinal travel. Thereby, with particular reference to FIG. 8, selective abutting engagement of a distal frictional surface, depicted as a toothed recess 216 distally projecting from the articulation locking member 111 is engaged to a corresponding locking gear segment 217 in a brake plate 218 received into a top proximal recess 220 of the articulating frame member 114. Distal and proximal holes 221, 222 in the brake plate 218 receive distal and proximal pins 223, 224 that upwardly project from the top proximal recess 220.

Figure 6:
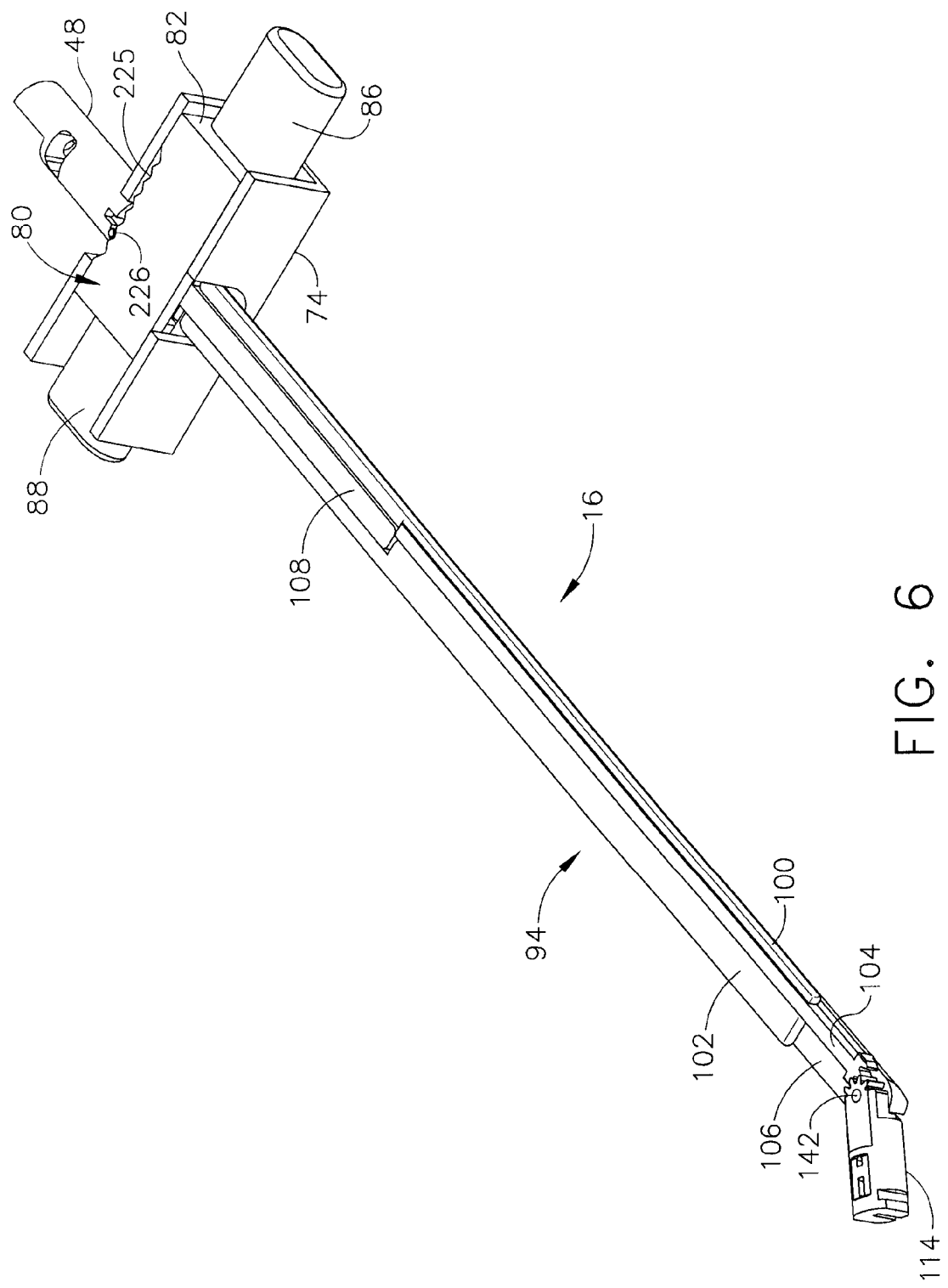
FIG. 6 is a front perspective view of an implement portion of the surgical instrument of FIG. 1 with a double pivot closure sleeve assembly and end effector removed to expose a single pivot frame ground articulated by a fluidic articulation mechanism.

With particular reference to FIG. 6, the elongate shaft 16 is depicted in an articulated position with the closure sleeve assembly 46 removed from around the frame assembly 44 and without the elongate channel 40 and anvil 42. Articulation actuator 80 is shown moved laterally to the left to compress right proximal reservoir bladder 90 and expanded distal right actuation bladder 100 moving T-bar 104 to the position shown. Thus, lateral movement of the articulation actuator 80 articulates the distal frame 114 clockwise about the single pivot frame ground 48 as shown. The articulation actuator 80 advantageously also automatically engages and disengages the articulation lock mechanism 200. In particular, a toothed detent surface 225 along a proximal top surface of the articulation actuator 80 receives an upwardly projecting locking pin 226 from the proximal end 204 of the articulation locking member 111. The engagement of the locking pin 226 within the root of the toothed detent surface 225 provides sufficient distal movement of the articulation locking member 111 for locking engagement of the locking gear segment 217 in the brake plate 218. Lateral movement by an operator of the compression member 272 proximally urges the locking pin 226 proximally, and thus disengages the articulation locking member 111 from the brake plate 218. When the operator releases the articulation actuator 80, the locking pin 226 is urged by the compression spring 202 into the adjacent detent in detent surface 225 to lock the locking mechanism 111, and thereby the staple applying assembly 20, constrains the articulation mechanism 14 at a desired articulation position by constraining and expanding the inflated shape of the proximal left and right reservoir bladders 90, 92.

Portions of the articulation lock mechanism 200 are described in greater detail in commonly-owned U.S. Pat. No. 5,673,841 A "SURGICAL INSTRUMENT" to Dale R. Schulze and Kenneth S. Wales, et al., filed 10 Mar. 1996, the disclosure of which is hereby incorporated by reference in its entirety.

Alternatively or additionally, an orifice may be provided within parallel fluid bladders 236, 238 to control the flow rate between the proximal actuating bladders 100,102 and distal reservoir bladders 90, 92. In FIGS. 16, 18, the fluid passageways 258, 264 may be sized to provide resistance to changing the angle of articulation, serving as the orifices or they may include a fluid flow rate limiting structure.

Figure 10:
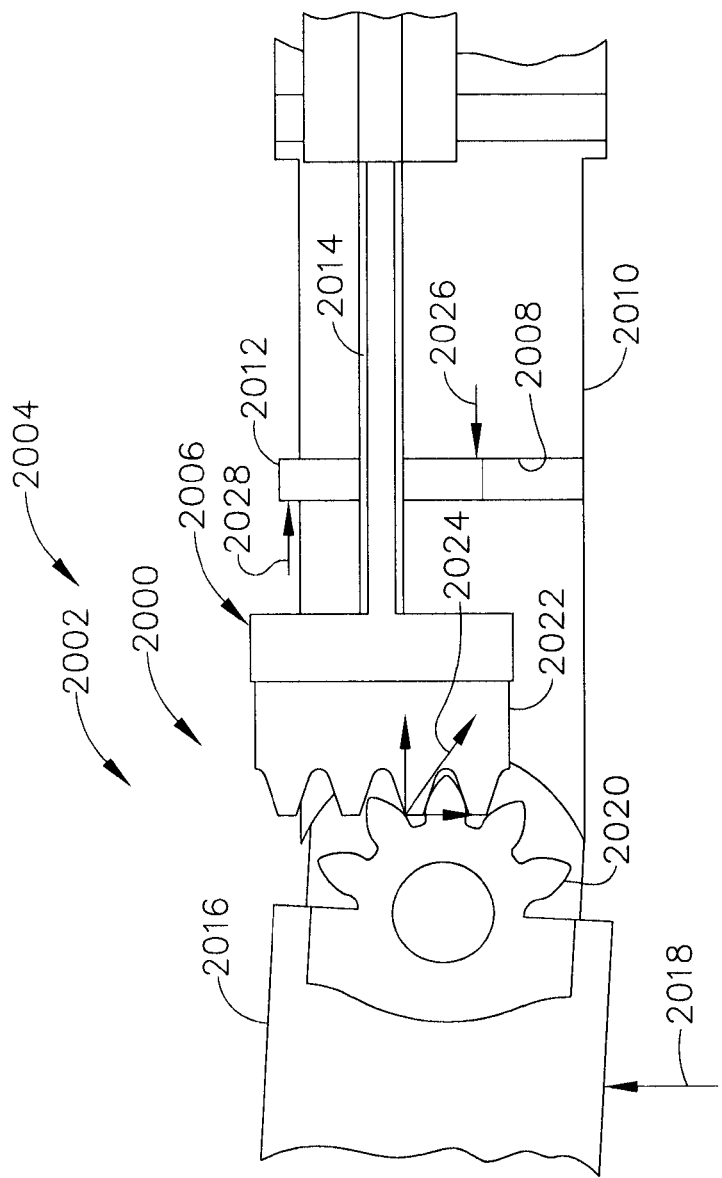
FIG. 10 is a top diagrammatic view of an alternate articulation locking mechanism for the surgical instrument of FIG. 1 with a closure sleeve assembly removed to expose a backloading disengaged T-bar for automatic articulation lock engagement and disengagement.

In FIG. 10, an alternate locking mechanism 2000 of an articulation mechanism 2002 of a surgical instrument 2004, is normally unlocked and is activated by cocking a laterally moving T-bar 2006 due to back loading. A slot 2008 is located in a frame ground 2010 to receive and guide a rib 2012 extending down from the T-bar 2006. A slender longitudinal section 2014, which is orthogonally attached to the rib 2012 deflects if an end effector 2016 is backloaded. For instance, as the end effector 2016 is forced to the right as depicted at arrow 2018, for instance, its proximal gear segment 2020 acts upon a rack 2022 of the T-bar 2006, imparting a nonorthogonal backdriving force, as depicted at arrow 2024. Thus, the slender longitudinal section 2014 bends, cocking rib 2012 in slot 2008. This cocking produces opposing binding forces, as depicted by arrows 2026, 2028, that lock the T-bar 2006 and prevent further articulation. Unlocking occurs when actuation of the articulation bladders uncocks the laterally moving T-bar 2006. Thereafter, the rib 2016 may assist in guiding the T-bar 2006.

Figure 11:
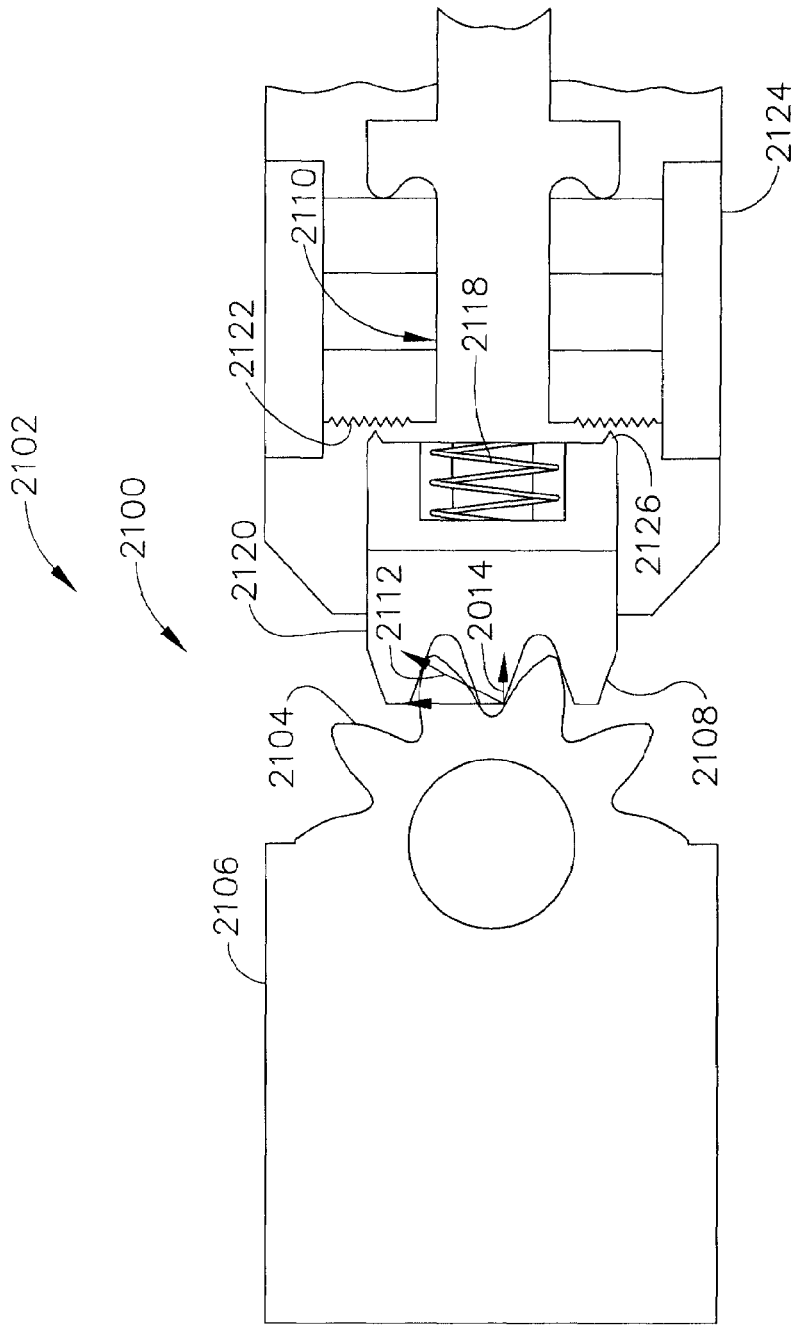
FIG. 11 is a top diagrammatic view of an additional alternative articulation mechanism for the surgical instrument of FIG. 1, a spring biased rack on a T-bar with locking features that engage due to backloading from an end effector.

In FIG. 11, yet an additional articulation locking mechanism 2100 for a surgical instrument 2102 is depicted that is normally unlocked and activated by the proximal force vector from the 20 degree pressure angle from gear teeth 2104 of an end effector 2106 and rack teeth 2108 of a T-bar 2110. When the end effector 2106 is backloaded, as depicted by nonorthogonal arrow 2112, the longitudinal vector of the pressure angle, depicted as arrow 2114, moves the T-bar 2110 proximally. This longitudinal force vector is applied to a stiff spring 2118 behind a rack 2120 of the T-bar 2110. When the spring 2118 deflects as T-bar 2110 moves proximally, locking teeth 2126 projecting proximally from the rack 2120 are brought into engagement while locking elements 2122 proximally and laterally aligned on a ground frame 2124 are brought into engagement with locking teeth 2126 projecting proximally from the rack 2120. The locking teeth 2126 and locking elements 2122 disengage when the proximal force vector is reduced or eliminated by removing the back loading of the end effector 2106 and allowing T-bar 2110 to move distally from urging from spring 2118.

Double Pivot Closure Sleeve and Single Pivot Frame Ground Combination

Figure 7:
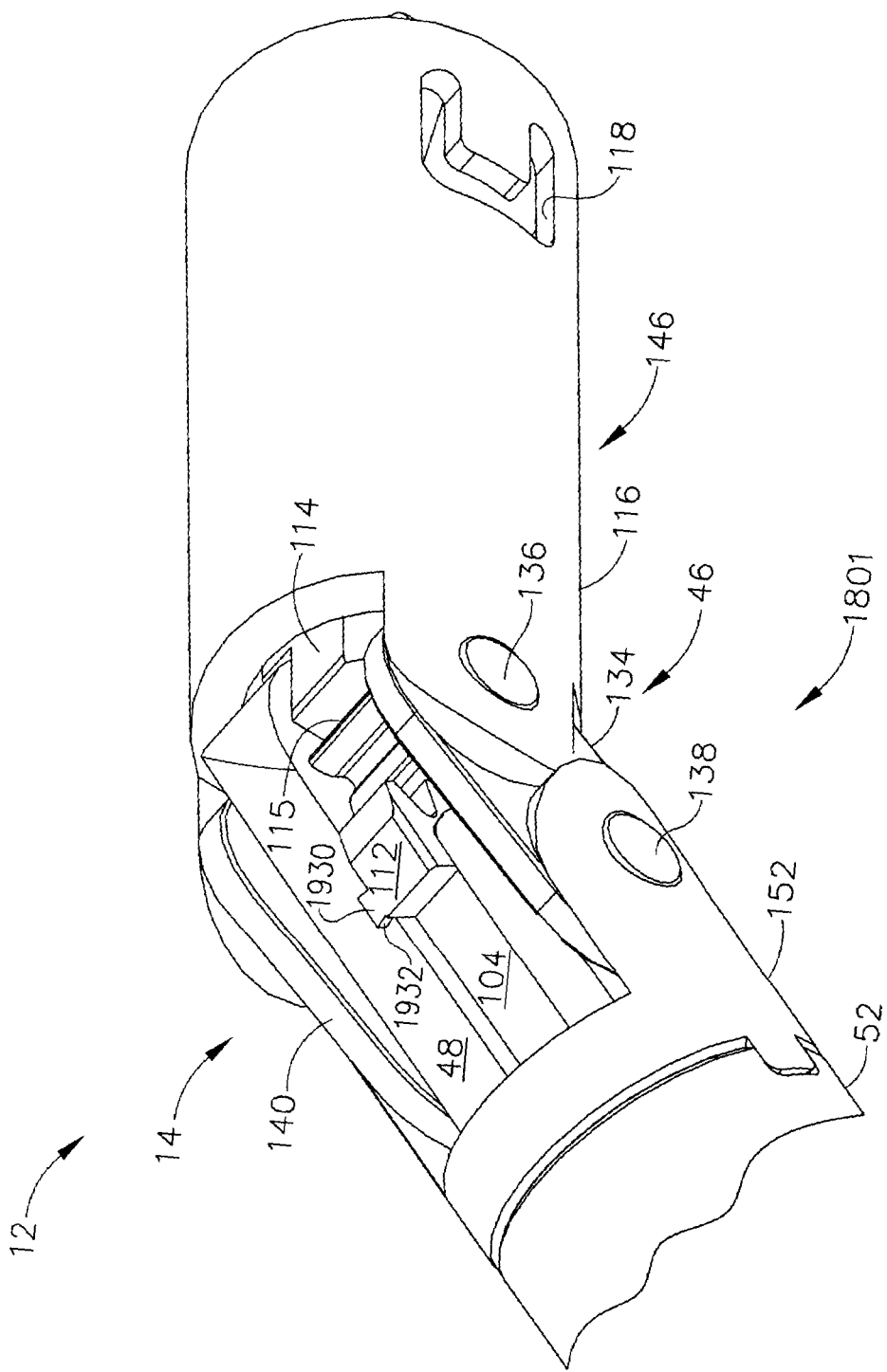
FIG. 7 is perspective detail view of an alternative articulation joint for the surgical instrument of FIG. 1 depicting a double pivoting closure sleeve assembly at a proximal position with a single pivot frame ground.

With reference to FIGS. 3–4 and 7, the implement portion 12 advantageously incorporates the double pivot closure sleeve assembly 46 that longitudinally translates over and encompasses a single pivot frame ground 48. These mechanisms and their operation will now be described in further detail. With particular reference to FIG. 7, the articulation mechanism 14 is depicted in an articulated state with the closure sleeve assembly 46 retracted proximally to an anvil open state. With the anvil 42 open, actuation of the articulation control 18 causes the articulated closure ring 116 to pivot about the upwardly directed distal pin 136 and downwardly directed distal pin 142 respectively of the upper and lower double pivot closure links 134, 140. The frame ground 48 pivots around a single pin, depicted as the proximal pin 1808 that joins frame ground 48 to distal frame member 114. With the anvil 42 open, the proximal pin 147 of frame ground 48 is aligned with the distal most position of upper and lower double pivot links 134, 140 of the closure sleeve assembly 46. This positioning allows easy pivoting and rotation of the staple applying assembly 20 while the anvil 42 is open. When the closure sleeve assembly 46 is moved distally to pivot anvil 42 closed, the closure straight tube 52 moves distally about frame ground 48 and the articulated closure ring 116 moves distally along the articulated distal frame member 114 axis as urged by pivot links 134, 140. Dual pivoting pins 136, 138 and 142, 144 on links 134, 140 facilitate engagement with closure straight tube 52 and articulated closure ring 116 as they are urged towards the distal closure position when the device is articulated (not shown). At the distal closure position, the frame ground pivot pin ("proximal pin") 147 is vertically aligned with proximal pivot pins 138, 144 at full articulation or may fall at any point between distal pins 136, 142 and proximal pins 138, 144 while working effectively.

Solid Firing Bar Support

Figure 8:
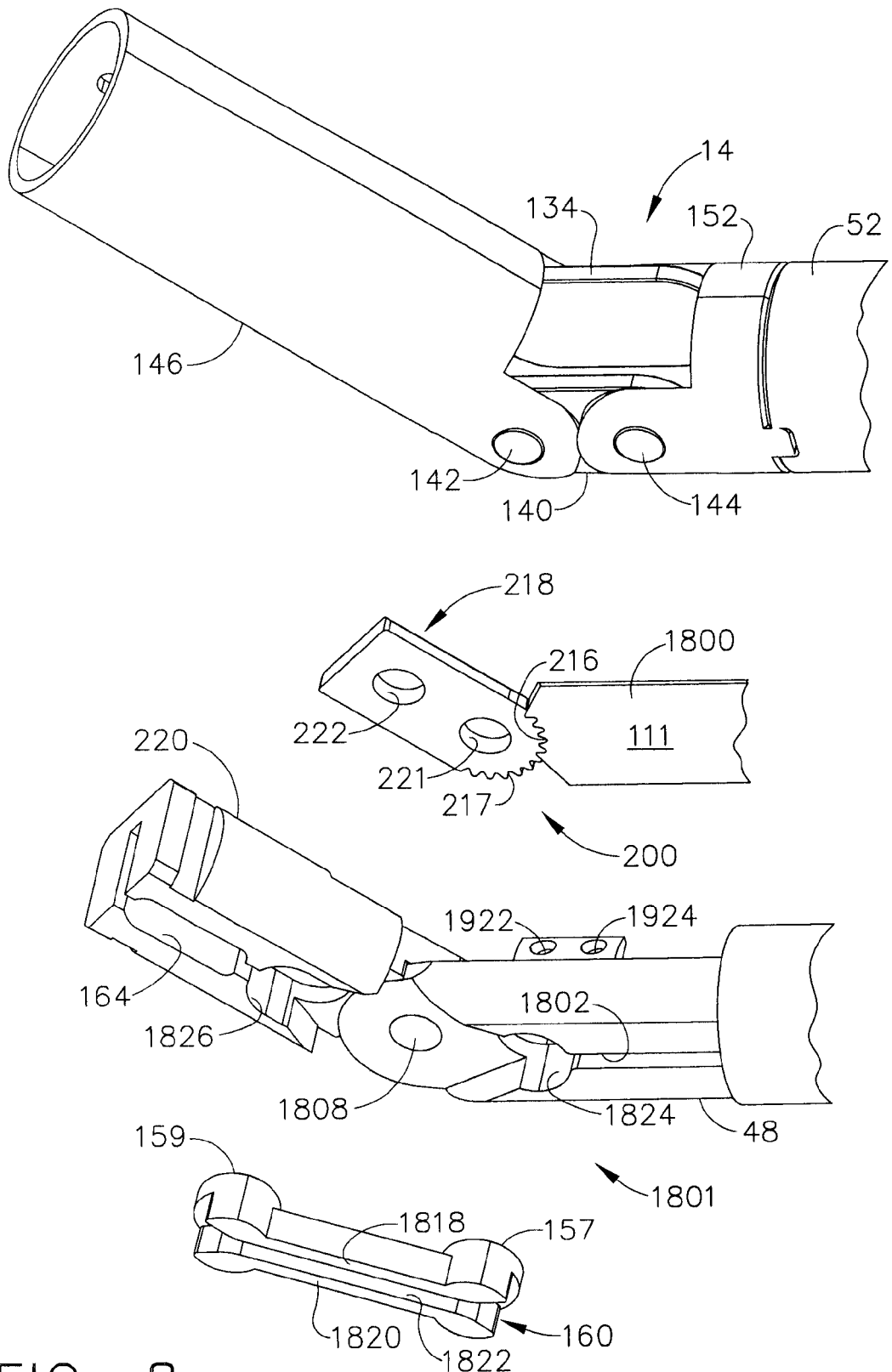
FIG. 8 is a bottom right perspective exploded view of the alternative articulation joint of FIG. 7 including a double pivoting fixed-wall dog bone link and a frame ground incorporating rail guides for a lateral moving member (T-bar).

In FIG. 8, the articulation mechanism 14 of FIG. 7 is partially exploded and viewed from the bottom, showing a solid wall firing bar support design (dog bone link 160) that offers advantages over conventional flexible support plates. Support plates are used to bridge the gap and guide and support the firing bar 66 through a single frame ground pivot articulation joint 1801. Flexible firing bars are known, but the incorporation of solid wall firing bars such as those shown in FIGS. 4, 8 and 9 offer unique advantages. Referring now to FIG. 8, frame ground 48 includes a frame knife slot 1802 that runs along the bottom of frame ground 48 and a distal knife slot 164 runs along the bottom of an articulating distal frame member 114 for the sliding reception of the firing bar 66 (not shown) therein. Frame ground 48 is described above and includes a direct single pivotal connection 1808 with the distal frame member 114. The fixed wall dog bone link 160 that is rotatably connected on proximal pin end 157 and movably connected on distal pin end 159 includes left and right lateral guides 1818, 1820, defining therebetween a guidance slot 1822 for sliding passage of a firing bar 66 (FIG. 4).

Thus, to bridge the gap between frame ground 48 and the distal frame member 114, the fixed wall pivoting dog bone link 160 is pivotally attached to frame ground 48 and is slidingly attached to frame member 114. Proximal pin 157 of the pivoting dog bone 160 is pivotally received in a bore 1824 in frame ground 48 enabling pivotal dog bone 160 to pivot about pocket bore 1824. The distal pin 159 extends upwards from pivotal dog bone 160 and is slidingly received in a slot 1826 in distal frame 114. Articulation of staple applying assembly 20 to an angle of such as 45 degrees from the longitudinal axis pivots pivoting dog bone 160 in bore 1824 at its proximal pin 157, and distal pin 159 slides into slot 1826 at its distal end 1814 to bend firing bar 66 to two spaced-apart angles that are half of the angle of the staple applying assembly 20. Unlike previously referenced flexible support plates that bend the firing bar 66 to a 45 degree angle, the fixed wall pivoting dog bone 160 bends the firing bar 66 to two spaced-apart angles of such as 22.5 degrees each. Bending the flexible firing bar or bars 66 to half the angle cuts the bend stress in the firing bars 66 to one-half of that found in conventional articulation supports. Reducing the bending stress in the firing bars 66 reduces the possibility of permanently bending or placing a set in the firing bars, reduces the possibility of firing jams, ensures lower firing bar retraction forces, and provides smoother operation of the firing system.

Figure 9:
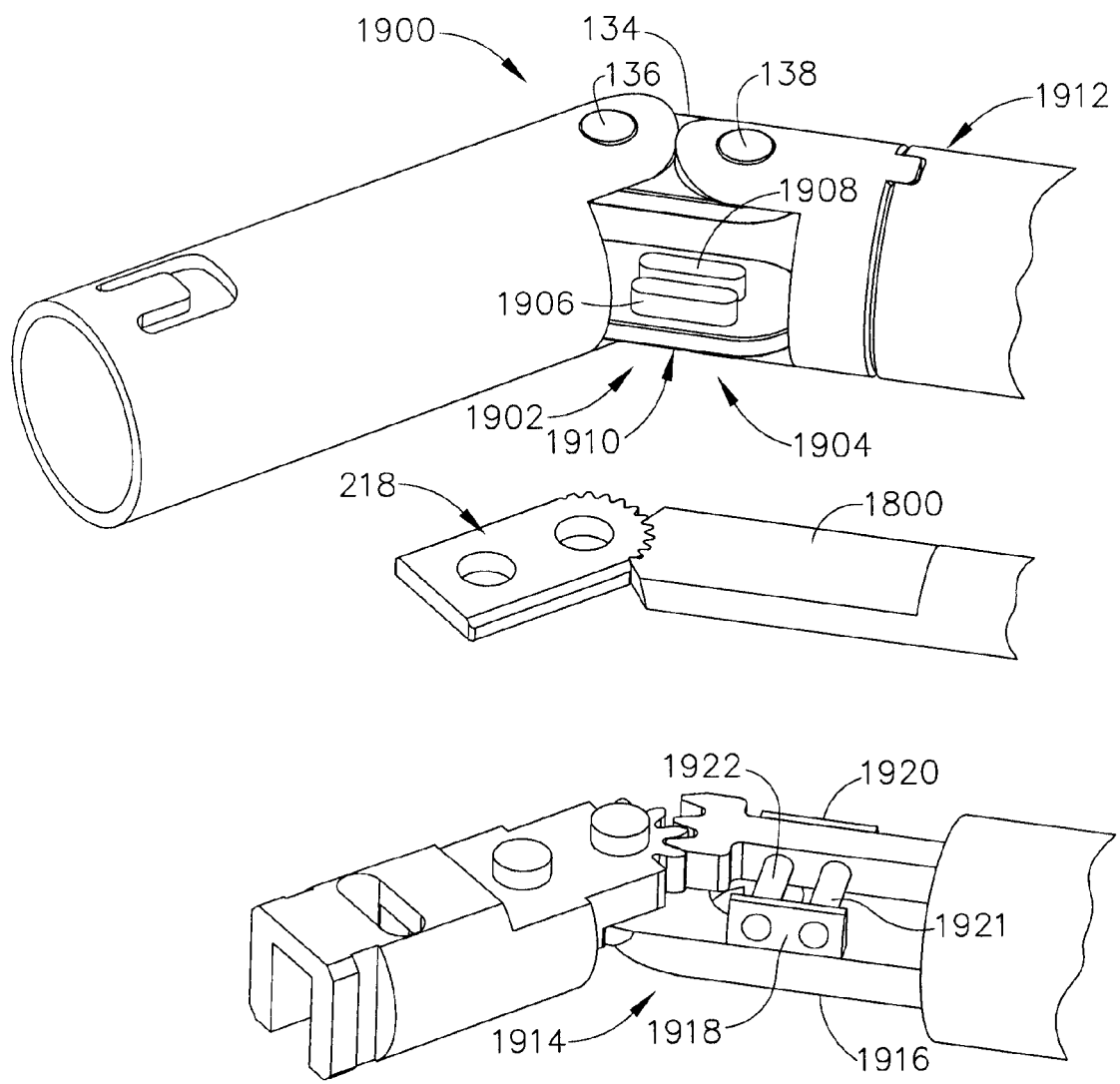
FIG. 9 is top left perspective exploded view of a further alternative articulation joint for the surgical instrument of FIG. 1, including an alternate solid wall support plate mechanism incorporated into a lower double pivot link to support a firing bar and includes a rail guided laterally moving member (T-bar).

In FIG. 9, a surgical instrument 1900 includes double closure pivot. Single frame pivot articulation joint 1902 shows an alternate solid wall support plate mechanism 1904 that replaces the lower double pivot link 140 and dog bone link 1812. Left and right firing bar supports 1906, 1908 extend upwardly from a lower double pivot link 1910 of a closure sleeve assembly 1912. Clearance 1914 is provided in a frame ground 1916 for the firing bar supports 1906, 1908 to travel as the closure sleeve assembly 1912 moves distally to close the anvil 42 (not shown in FIG. 9) and proximally to open anvil 42. Like the above described pivoting dog bone 1812, the alternate lower double pivoting link 1910 also bends and supports the firing bar 66 (not shown in FIG. 9) creating two spaced apart bend angles that are up to one-half of the bend angle of the staple applying assembly 20.

Lateral Member Guide Mechanisms

Figure 12:
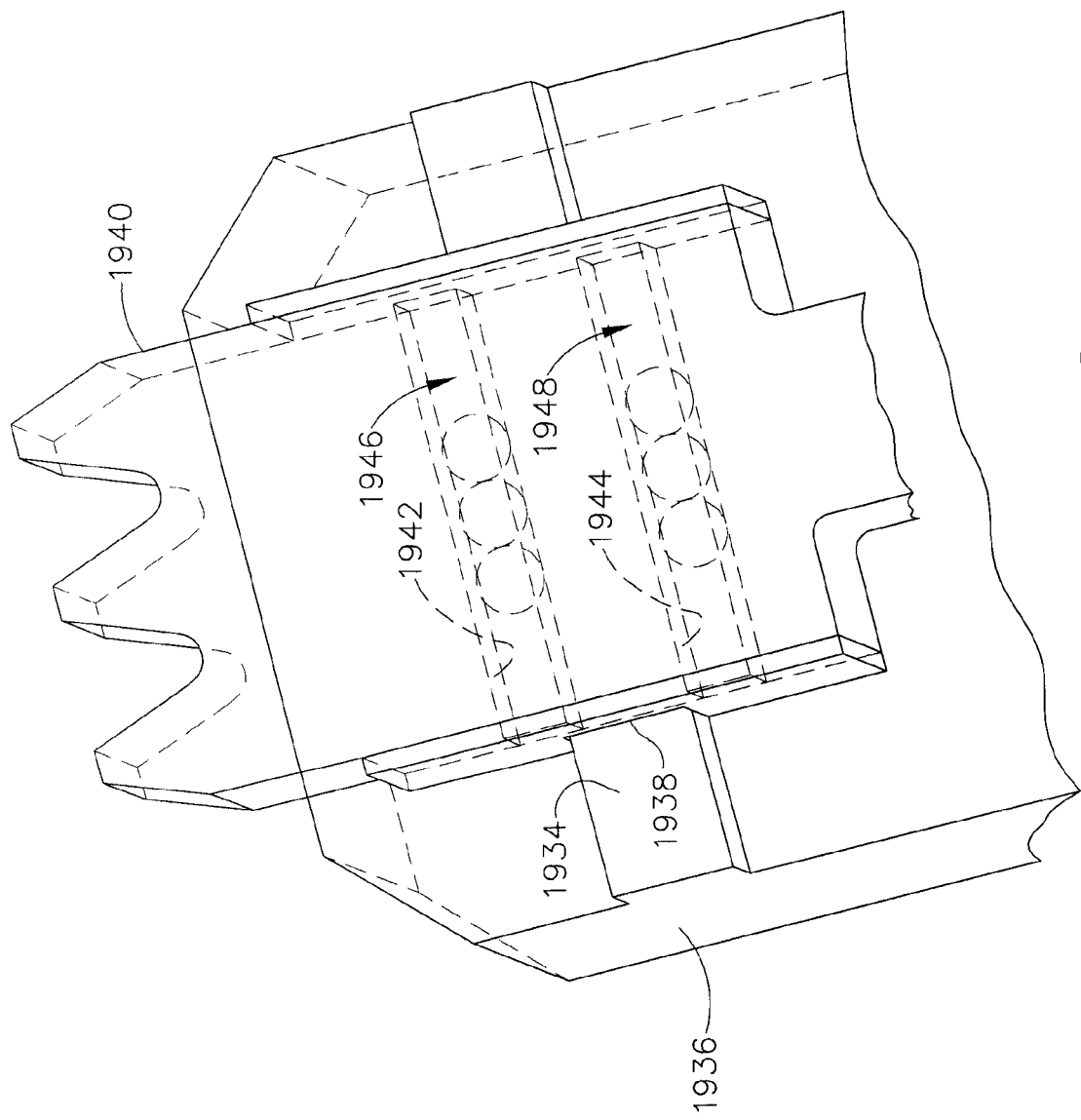
FIG. 12 is an alternative T-bar and frame ground incorporating lateral guidance for the surgical instrument of FIG. 1.
Figure 13:
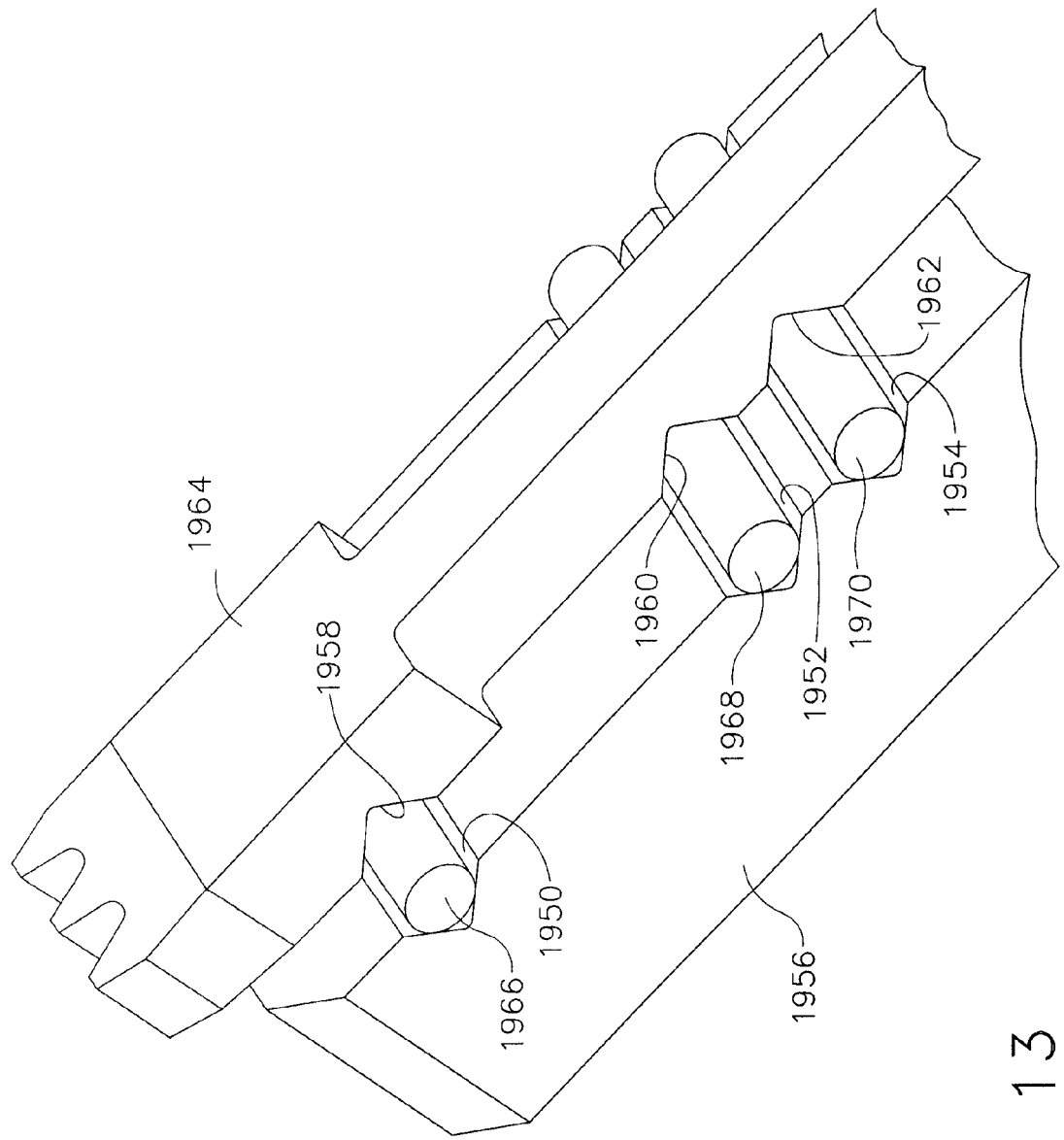
FIG. 13 is yet an additional alternative T-bar and frame ground incorporating lateral guidance for the surgical instrument of FIG. 1.

With further reference to FIG. 9, left and right upward flanges 1918, 1920 on the frame ground 1916 include distal and proximal lateral pin guides 1922, 1924 that pass laterally through holes in a T-bar 1926 assisting in minimizing binding in an articulation mechanism 1928. As another example, in FIG. 7, the T-bar 104 advantageously included a dovetail lateral guide 1930 that laterally slides within a dovetail channel 1932 formed therein. As yet a further example, in FIG. 12, a raised rib 1934 on a frame ground 1936 is received within a rectangular slot 1938 formed in a T-bar 1940. To further facilitate non-binding lateral translation, distal and proximal lateral bearing tracks each include a respective plurality of ball bearings 1946, 1948. As yet a further example, in FIG. 13, a plurality of frame lateral grooves 1950–1954 are formed in a frame ground 1956 with corresponding T-bar lateral grooves 1958–1962 in a T-bar 1964. Slide rollers 1966-1970 reside trapped within respective pairs of lateral grooves 1950/1958, 1952/1960, 1954/1962. These are by no means an exhaustive list of lateral guidance members that prevent unwanted cocking or rotation of the T-bar 1940.

Double Pivot Frame Ground and Single Pivot Closure Combination

Figure 14:
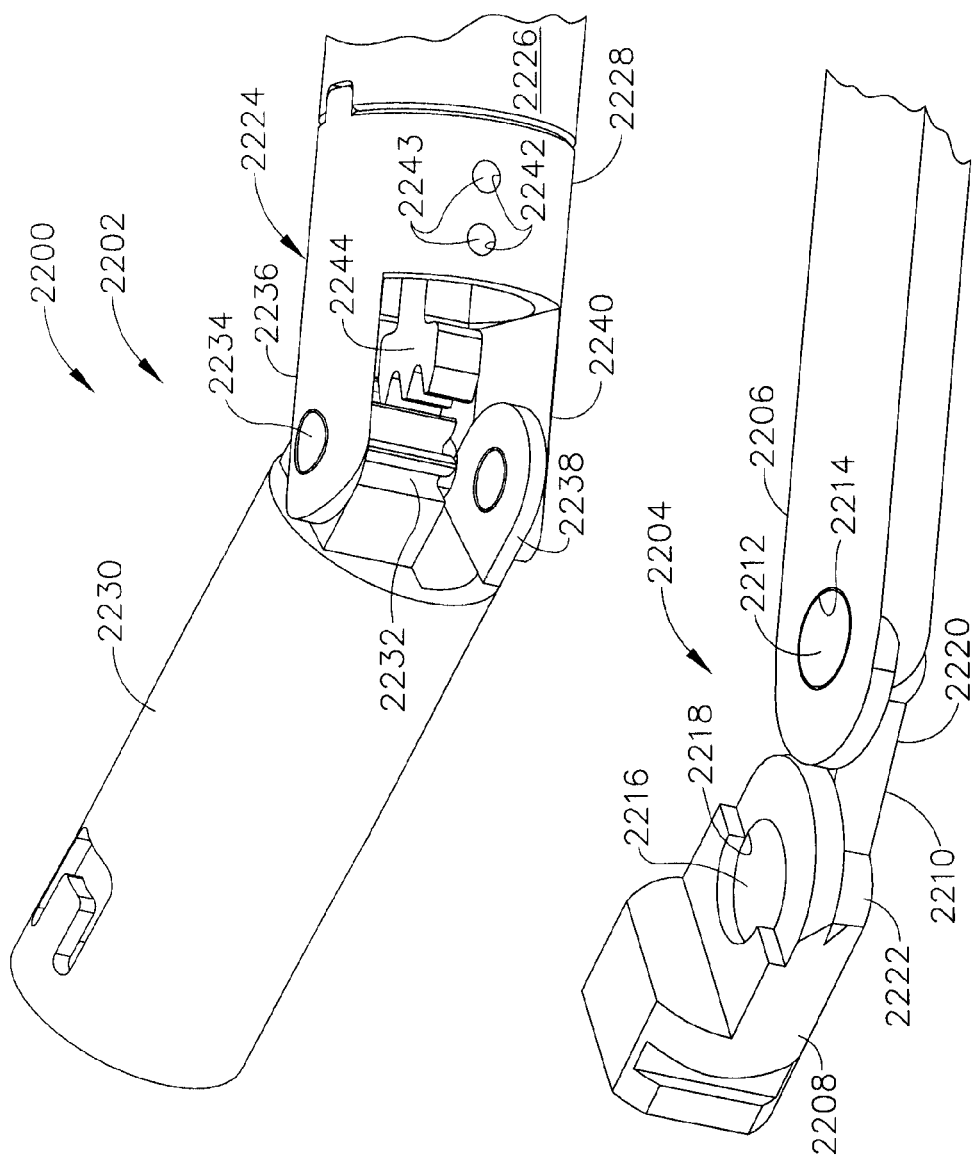
FIG. 14 is a left top perspective disassembled view of an alternative articulation mechanism including a double pivoting frame assembly and single pivoting closure sleeve assembly for the surgical instrument of FIG. 1.
Figure 15:
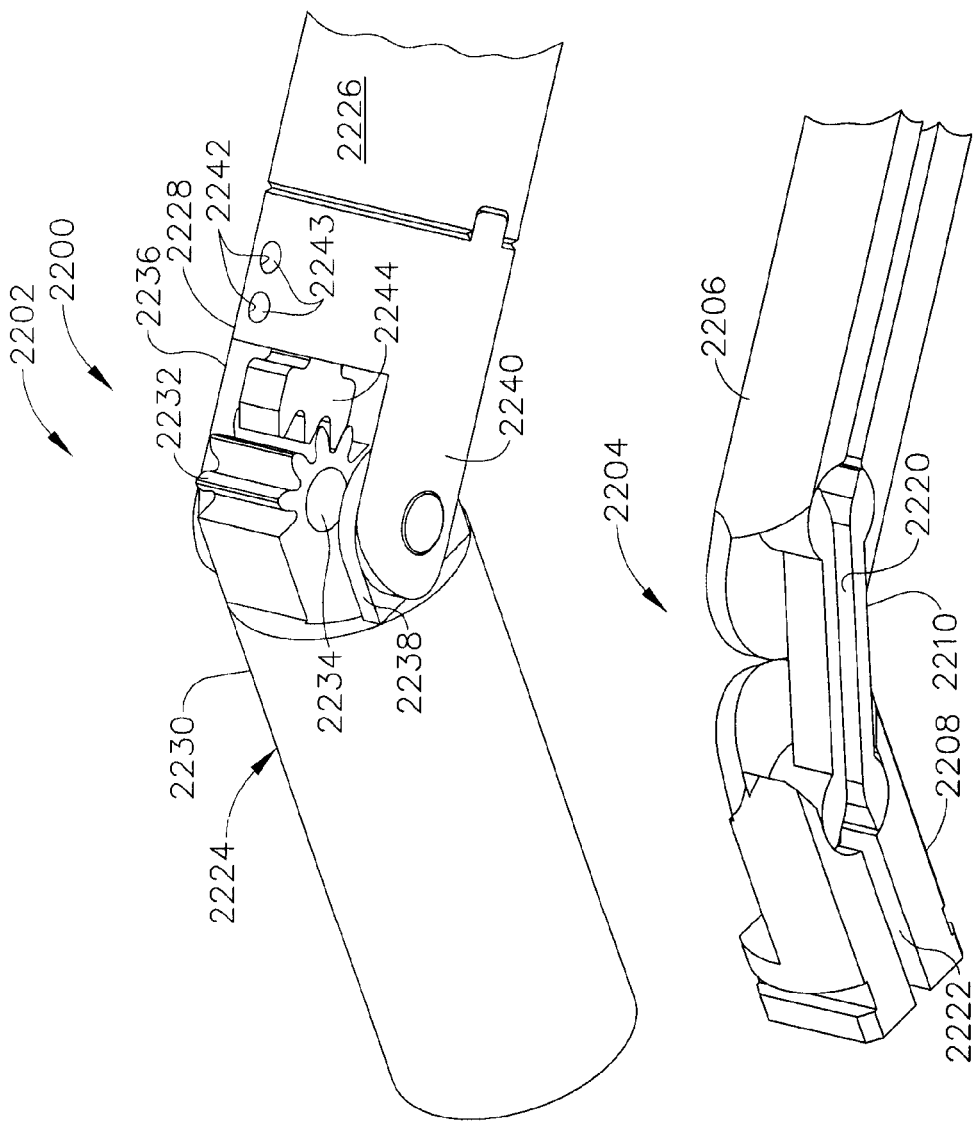
FIG. 15 is a left bottom perspective view of the alternative articulation mechanism of FIG. 14.

In FIGS. 14–15, an alternate frame ground and closure mechanism 2200 includes a surgical instrument 2202 that includes double pivoting frame assembly 2204. In particular, a frame ground 2206 is connected to distal frame member 2208 by a dual pivot frame dog bone 2210 having a proximal pivot pin 2212 pivotally engaging a proximal bore 2214 in frame ground 2206 and a distal pivot pin 2216 engaging a distal bore 2218 of distal frame member 2208. A guidance slot 2220 is located on the underside of dog bone 2210 for the guidance of a firing bar 66 (not shown in FIGS. 14–15) therein. Knife slot 2222 is located in distal frame member 2208. As shown, articulation of the closure ring 2230 to a 45 degree angle articulates distal frame member 2208 to a 45 degree angle and articulates frame dog bone 2210 to half that angle. Consequently, firing bar 66 is subjected to the two shallow half bends that are spaced apart and obtains all the benefits listed above.

Outermost closure sleeve assembly 2224 is different in that only one pivot axis of the double pivoting design of the frame assembly 2204 accommodates its longitudinal closure motion. As shown, a closure tube shaft 2226 has a clevis 2228 at a distal end. Clevis 2228 is pivotally engaged with a closure ring 2230. Closure ring 2230 has a proximal gear 2232 formed at a distal end and pin 2234 pivotally engages an upper tang 2236 of clevis 2228 and a lower arm 2238 engages with a lower tang 2240 of clevis 2228. Holes 2242 in the clevis 2228 receive lateral guides pins 2243 and slidably attach a T-bar 2244 therein to engage proximal gear 2232 of the closure ring 2230. Thus, this alternate mechanism 2200 uses a reversed single/dual pivot alternate concept from the previously described mechanism. That is, the alternate closure mechanism has a single pivot and the alternate frame ground has a dual pivot, unlike the previously described dual pivot closure mechanism with a single pivot frame ground.

Laterally Moving Articulation Mechanism

In FIGS. 16–19, a laterally moving articulation mechanism 230 is depicted schematically to show lateral motion being used to effect articulation of an end effector 232. Lateral motion is the movement of at least one element toward or away from the longitudinal axis of a surgical device 234. This motion is generally at right angles to the longitudinal axis, which is a horizontal line bisecting the mechanism 230, and does not involve rotational motion or longitudinal motion. Laterally moving articulation mechanisms can be fluid actuated as shown in FIGS. 16–19 or mechanically actuated as shown in FIGS. 20–23.

Laterally Moving Fluid Articulation Mechanism

The laterally moving articulation mechanism 230 is shown schematically in FIGS. 16–19 and includes a fluid control system 235 having fluid-filled parallel left and right fluid bladders 236, 238 extending longitudinally therein that move a lateral member or T-bar 240 laterally by the movement of fluids 242. All directions are in reference to the longitudinal axis. Referring to the unarticulated view of FIGS. 16 and 17, the distally located end effector 232 pivots about pin 244 and has a gear segment 246 at a proximal end. Pivot pin 244 is attached to a frame (not shown). A rack 248 at a distal end of the T-bar 240 operably engages gear segment 246. T-bar 240 and rack 248 are laterally moveable along axis A—A. A distal portion of the long left and right fluid bladders 236, 238 lie laterally to the laterally moveable T-bar 240 and are laterally constrained within a closure sleeve 250 and vertically constrained by a frame 252 below and a spacer 254 above. Left actuating fluid bladder 236 is filled with fluid 242 and has left distal actuating bladder 256, left fluid passageway 258, and a left proximal reservoir bladder 260. Right fluid bladder 238 contains fluid 242 and has a right distal actuating bladder 262, right fluid passageway 264, and right proximal reservoir bladder 268. A fixed divider 270 extends from the frame 252 and separates the bladders 260, 268 and the fluid passageways 258, 264. The fixed divider 270 and the closure sleeve 250 constrain the fluid passageways 258, 264 and prevent expansion in the fluid passage sections 258, 264 of the bladders 236, 238. A laterally moveable "C" shaped compression member 272 is included in articulation control mechanism 230 for the compression of one of the proximal reservoir bladders 260, 268 and the articulation of the end effector 232. In addition, other components such as a firing bar 274 passing through a firing bar slot 276 in the frame 252 may be incorporated (FIGS. 17, 19).

As shown in FIGS. 2 and 18–19, lateral movement of C-shaped compression member 272 to the left compresses right proximal reservoir bladder 260 forcing fluid into right fluid passageway 258 and right distal actuating bladder 256. As right distal actuating bladder 256 moves T-bar 240 laterally to the left, the left distal actuating bladder 262 is compressed and the end effector 232 is articulated to the right (clockwise as viewed from the top as shown). Compression of the left distal actuating bladder 262 causes fluid to flow proximally through the left fixed fluid passageway 264 and into left proximal reservoir bladder 266. In particular, an attached right wall 280 of the C shaped compression member 272 moves to the left causing compression of the right proximal reservoir bladder 260. A corresponding movement left of an attached left wall 278 of the C shaped compression member 272 provides space for the fluid from compressed left reservoir bladder 262 as the fluid flows into the expanding left proximal reservoir bladder 266.

This fluid control system 235 for the articulation mechanism 230 offers at least several advantages. First, the orientation of the actuating bladders 256, 262, proximal to the articulation joint or mechanism 230, allows the use of long bladders 236, 238 and longer T-bars 240 within the instrument 234. As a fluid-driven system, increasing the output force of the fluid control system 235 may be accomplished in two ways. First, for a fixed fluid area on the T-bar 240, the fluid pressure onto the fixed area may be increased. Second, for a fixed fluid pressure, the fluid contact area on the T-bar 240 may be increased. The first method results in a more compact design and higher system pressures. The second method results in a larger design and lower system pressures. To decrease cost, simplify the design, reduce system stress, and reduce risk of bladder rupture, the illustrative version depicts long distal actuating bladders 256, 262 in an advantageous position proximal to the articulation mechanism 230 within an elongate shaft of the instrument. It is this placement of the bladders 256, 262 that enable the bladders 256, 262 to be long and the articulation output force to be high for a low input pressure.

Thus, the output force of the articulation mechanism 230 can be increased (for the same input pressure) simply by increasing the pressure contact area of the distal balloons 256, 262 on T-bar 240. Pressure contact area increases are restricted to height and length. Since the diameter of conventional endoscopic surgical instruments are fixed at certain diameters to pass through insufflation ports, this limits the height change. Changing the length of the pressure contact area has the greatest effect and enables the lateral output force of the device to be advantageously tuned (by changing length) to meet whatever output force the system requires.

Fluids used in a laterally moving device can be either compressible or incompressible. As used herein, the term "fluid" comprises liquids, gases, gels, microparticles, and any other material which can be made to flow between a pressure gradient. While any fluid can be used, sterilized solutions such as saline, mineral oil or silicone are especially preferred.

Laterally Moving Mechanical Articulation Mechanism

Whereas fluid mechanisms are described above to cause lateral movement and articulation, mechanical mechanisms may accomplish a similar lateral motion as produced by fluid bladders 206, 208. In FIGS. 20–21, an alternate laterally moving articulation mechanism 300 employs a mechanical control system, in particular a longitudinally moving member, to affect lateral motion and articulation for a surgical instrument 301. In the illustrative version, with particular reference to FIG. 20, a laterally moving slide bar 302 has at least one pair of angled left and right cam surfaces 304, 306 extending laterally therefrom on opposite sides of an elongate longitudinal shaft 308. In the illustrative version, another pair of proximal left and right angled cam surfaces 310, 312 are also included. A right longitudinally moving link 314 includes corresponding inwardly directed distal and proximal counter ramped surfaces 316, 318 that register and slidingly engage to distal and proximal right cam surfaces 306, 312 such that distal longitudinal movement of the moving link 312 causes leftward lateral movement of the slide bar 302. It should be appreciated that this ramping contact may be reversed such that distal movement causes rightward movement respectively.

It should be appreciated that a spring bias (not shown) may be included on the slide bar 302 to urge the slide bar 302 rightward into engagement with the right longitudinally moving link 314 so that the opposite proximal movement of the right longitudinal moving link 314 causes leftward movement of the slide bar 302. Alternatively, in the illustrative version, a left longitudinally moving link 320 includes corresponding inwardly directed distal and proximal counter ramped surfaces 322, 324 that register and slidingly engage to distal and proximal right cam surfaces 304, 310, the latter ramp distally and the former ramp proximally so that distal longitudinal movement of the left longitudinally moving link 320 causes rightward lateral movement of the slide bar 302. It should be appreciated that this ramping contact may be reversed such that proximal movement causes leftward movement. It should be appreciated that the right and left longitudinally moving links 314, 320 and sliding bar 302 are supported within an elongate shaft 326 that allows this longitudinal movement of the former and lateral movement of the latter.

A distal end of the slide bar 302, depicted as a socket ball 328, is received within a V-shaped cam groove 330 proximally aligned and proximal to a pivot pin 332 of an end effector 334. Thus, in FIG. 21, proximal movement of the right longitudinally moving link 314 and distal movement of the left longitudinally moving link 320 causes rightward movement of the sliding bar 302 with a corresponding rightward movement of the socket ball 328. Thus the V-shaped cam groove 330 is driven rightward, pivoting its most distal end 336 to the left. Alternatively, lateral movement of the slide bar 302 may be converted to articulation of the end effector 334 by the rack and gear engagement described above with respect to FIGS. 16–19. Thus, mechanical systems that use longitudinal movement can be used to provide lateral articulation for the surgical instrument 301.

Rotatable Link

Figure 23:
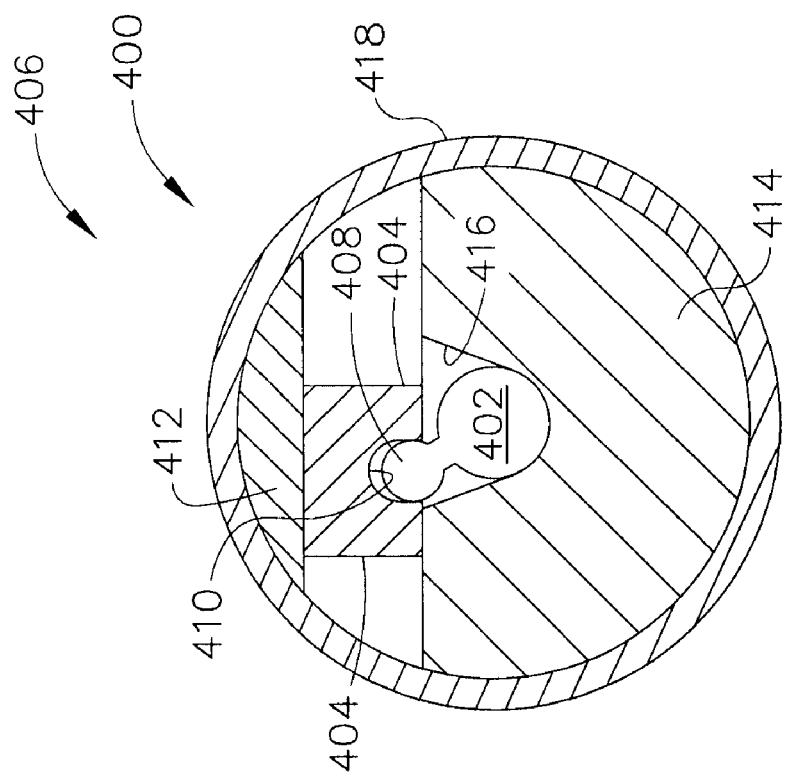
FIG. 23 is a front cross section view in elevation of the alternative rotary link mechanical control system of FIG. 22 in an articulated state.
Figure 22:
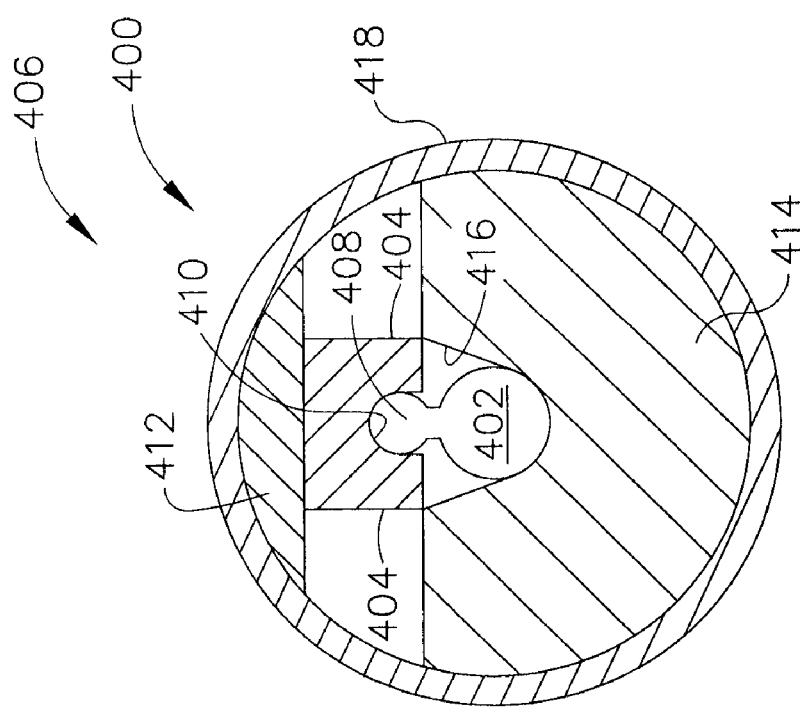
FIG. 22 is front cross section view in elevation of an alternative rotary link mechanical control system for a surgical instrument of FIG. 16 or 20 for laterally translating respectively a T-bar or slide bar, depicted in an unarticulated state.

In FIGS. 22 and 23, a further alternate articulation mechanism 400 uses a rotatable link 402 to move a lateral member, depicted as laterally moving slide bar 404, to cause articulation for a surgical instrument 406. The laterally moving slide bar 404 may operably engage with a rotary gear or a cammed groove as described above for FIGS. 16 and 20 at a proximal end of an end effector (not shown). Rotatable link 402 may be located below the slide bar 404 with at least one arm 408 extending rotatably transverse to the longitudinal axis therefrom to engage within a socket 410 within the slide bar. The slide bar 404 is vertically constrained between a top spacer 412 and a bottom frame 414, the later having a longitudinal trough 416 that receives the rotatable link 402 and accommodates rotation of the arm 408. The spacer 412 and frame 414 are encompassed by a tubular sleeve 418. Rotation of the rotary link 402 moves the arm 408 in an arc and thereby moves the slide bar 404 laterally in the direction of rotation.

Articulation Mechanism Having Opposing Buckling Flexible Members

In FIG. 24, a surgical instrument 500 has a slide member 502 aligned along a longitudinal axis of an elongate shaft 504 and allows lateral movement between a left buckling member 506 and a right buckling member 508 and is vertically constrained by a frame and spacer (not shown). Each buckling member 506, 508 has a respective fixed distal attachment 510, 512 and a longitudinally translatable proximal link 514, 516. Respective left and right flexible members 518, 520 inwardly bow in opposition against the slide bar 502, with the amount of lateral intrusion in relation to distal longitudinal movement of their respective proximal link 514, 516. In an unarticulated state shown in FIG. 24, the proximal links 514, 516 are not differentially positioned, and thus a distally projecting tip 522 of the slide member 502 is centered within a V-shaped cam groove 524 that proximally opens relative to a pivot pin 526 of an end effector 528. In FIG. 25, the left proximal link 514 has been distally advanced and the right proximal link has been proximally retracted, causing the slide bar 502 to laterally translate to the right, thereby causing camming of the distally projecting tip 522 against a right portion of the V-shaped cam groove 524 with resultant leftward articulation of the end effector 528 about the pivot pin 526.

Electromagnetic Lateral Articulation Control Mechanism

Figure 26:
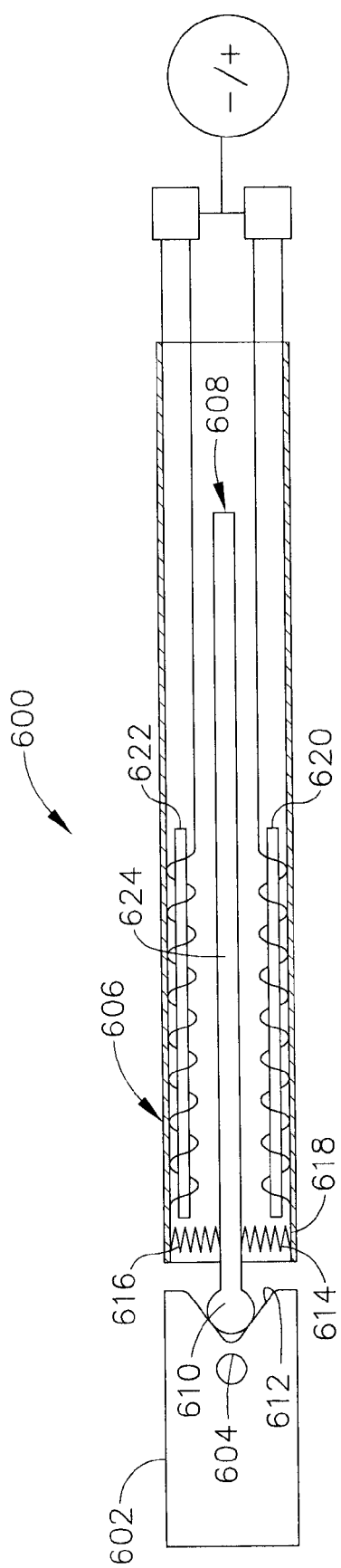
FIG. 26 is a top diagrammatic view of a surgical instrument having an electromagnetic lateral articulation control mechanism.
Figure 27:
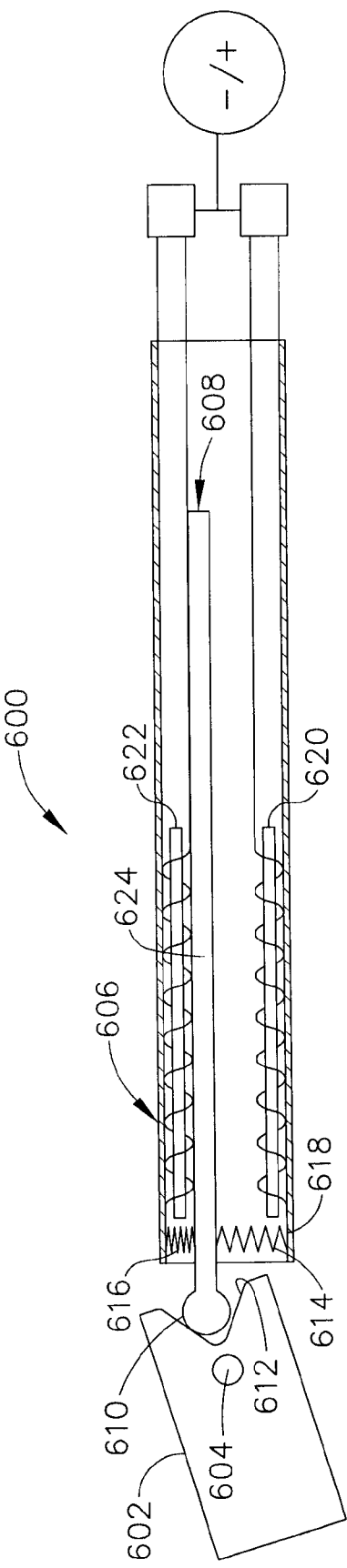
FIG. 27 is a top diagrammatic view of the surgical instrument of FIG. 26 in an articulated state.

In FIG. 26, a surgical instrument 600 has a distally connected end effector 602 that is selectively articulated in an arc about its pivot pin 604 relative to an elongate shaft 606 by lateral motion of a slide bar 608. In particular, a distal socket 610 of the slide bar 608 engages a V-shaped cam groove 612, opening proximal to the pivot pin 604. The slide bar 608 is vertically constrained within the elongate shaft 606 by a frame and spacer (not shown). Left and right compression springs 614, 616 that are inwardly directed on opposite lateral sides of the slide bar 608 are proximate to a distal end 618 of the elongate shaft 606. These springs 614, 616 provide a centering bias on the slide bar 608 and thus on the end effector 602. Left and right electromagnets 620, 622 on opposing sides of the slide bar 608 are selectively activated to attract a ferrous target 624 integral or affixed to the slide bar 608, thereby selectively displacing the slide bar 608 laterally and effecting articulation of the end effector 602, as depicted in FIG. 27. For simplicity, a longitudinally-aligned coil is depicted, although it should be appreciated that one or more electromagnets may be aligned to produce a magnetic field perpendicular to the slide bar 608, such as a plurality of coils (not shown) aligned along the longitudinal length of the slide bar 608 with each coil having its longitudinal axis aligned with the lateral movement axis of the slide bar 608.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For instance, a single fluid transfer approach may be incorporated wherein a single fluid actuator expands and compresses to effect articulation, perhaps assisted by a resilient opposing member that is not in fluid or pneumatic communication to the handle. An application consistent with such a design, for instance, could include just one bladder attached to a T-bar so that when compressed by the withdrawal of fluid, it pulls the T-bar with it.

What is claimed is:

1. A surgical instrument, comprising:
an end effector including a proximal camming surface;
an elongate shaft, wherein the elongate shaft defines a longitudinal axis, the elongate shaft further including a frame defining a lateral recess aligned with the longitudinal axis, wherein the lateral recess is proximate to a distal end of the elongate shaft;
an articulation joint pivotally attaching the end effector to the distal end of the elongate shaft comprising a pivot axis distal to the proximal camming surface;
a slide bar sized for lateral movement within the lateral recess and having a distal portion engaged to the proximal camming surface of the end effector to effect articulation of the end effector, wherein the slide bar is movable laterally relative to the longitudinal axis to effect articulation of the end effector;
a lateral guide mechanism engaging the slide bar to the frame, wherein the lateral guide mechanism is operable to move the slide bar laterally relative to the longitudinal axis while maintaining parallel alignment of the slide bar to the longitudinal axis of the elongate shaft; and
a handle portion proximally attached to the elongate shaft and operably configured to produce an articulation motion to laterally move the slide bar;
wherein the proximal camming surface of the end effector comprises a gear segment and the distal portion of the slide bar comprises a gear rack;
wherein the lateral guide mechanism comprises a channel formed laterally in the frame and a rib received in the channel, perpendicularly attached to the slide bar further comprising a flexible longitudinal portion connecting the rib to the gear rack, wherein manipulating the end effector causes backdriving of the gear segment that flexes the longitudinal portion, cocking the rib into binding engagement in the channel.

2. The surgical instrument of claim 1, wherein the proximal camming surface of the end effector comprises a proximally directed camming recess that receives the distal portion of the slide bar.

3. The surgical instrument of claim 1, wherein the lateral guide mechanism engaging the slide bar to the frame for lateral and longitudinally aligned movement of the slide bar comprises a rotatable link aligned parallel to the slide bar and aligned with a vertical centerline of the shaft, the rotatable link pivotally joined to a near surface of the slide bar causing lateral movement thereof as the rotatable link rotates.

4. The surgical instrument of claim 3, wherein the rotatable link includes a plurality of pivotal joinings to the slide bar spaced along a longitudinal length thereof to maintain the alignment during actuation.

5. The surgical instrument of claim 1, wherein right and left distal fluid actuated bladders are placed on respective sides of the slide bar, the handle portion including an articulation control operatively configured to differentially transfer fluid to the right and left distal fluid actuated bladders, wherein the left and right distal fluid actuated bladders together have a combined volume, wherein the combined volume of both the left and the right distal fluid actuated bladders remains constant as fluid is transferred from one to the other to move the slide bar in a selected lateral direction.

6. The surgical instrument of claim 1, wherein right and left mechanical actuators are placed on respective sides of the slide bar, the handle portion including an articulation control operatively configured to exert differential longitudinal motions to the right and left mechanical actuators to laterally displace the slide bar.

7. A surgical instrument, comprising:
- a staple applying assembly, wherein the staple applying assembly has a proximal camming surface;
- an elongate shaft attached to the staple applying assembly, wherein the elongate shaft defines a longitudinal axis, the elongate shaft further including a frame defining a recess aligned with the longitudinal axis;
- an articulation joint pivotally attaching the staple applying assembly to a distal end of the elongate shaft;
- a slide bar within the recess, wherein the slide bar is movable laterally relative to the longitudinal axis, the slide bar having a distal portion engaged to the proximal camming surface of the staple applying assembly, wherein the slide bar is positioned to impart an articulation rotation to the end effector in proportion to a lateral position of the slide bar within the recess;
- right and left actuators on respective sides of the slide bar in the recess, wherein the right and left actuators are operable to move the slide bar laterally relative to the longitudinal axis to selectively laterally position the slide bar within the recess of the elongate shaft;
- a means for laterally guiding the slide bar within the recess defined by the frame, maintaining the slide bar in parallel alignment with a longitudinal axis of the shaft during lateral movement of the slide bar relative to the longitudinal axis in response to the actuators; and
- a handle portion proximally attached to the elongate shaft and operably configured to produce differential longitudinal motions to respective actuators to laterally move the slide bar relative to the longitudinal axis,
- wherein the proximal camming surface of the staple applying assembly comprises a gear segment and the distal portion of the slide bar comprises a gear rack;
- wherein the means for laterally guiding the slide bar comprises a channel formed laterally in the frame and a rib received in the channel, perpendicularly attached to the slide bar further comprising a flexible longitudinal portion connecting the rib to the gear rack, wherein manipulating the staple applying assembly causes backdriving of the gear segment that flexes the longitudinal portion, cocking the rib into binding engagement in the channel.

* * * * *